(12) United States Patent
Metzler-Nolte et al.

(10) Patent No.: US 11,267,831 B2
(45) Date of Patent: Mar. 8, 2022

(54) EF-TU-BINDING METAL-CONTAINING ANTIBIOTIC

(71) Applicant: Ruhr-Universitaet Bochum, Bochum (DE)

(72) Inventors: Nils Metzler-Nolte, Bochum (DE); Daniel Siegmund, Herten (DE); Julia Bandow, Witten (DE); Sina Schaekermann, Wetter (DE)

(73) Assignee: Ruhr-Universitaet Bochum, Bochum (DE)

( * ) Notice: Subject to any disclaimer, the term of this patent is extended or adjusted under 35 U.S.C. 154(b) by 50 days.

(21) Appl. No.: 16/629,044

(22) PCT Filed: Jun. 18, 2018

(86) PCT No.: PCT/EP2018/066100
§ 371 (c)(1),
(2) Date: Jan. 7, 2020

(87) PCT Pub. No.: WO2019/007664
PCT Pub. Date: Jan. 10, 2019

(65) Prior Publication Data
US 2020/0199162 A1 Jun. 25, 2020

(30) Foreign Application Priority Data
Jul. 7, 2017 (DE) .......................... 102017115215.6

(51) Int. Cl.
*C07F 13/00* (2006.01)
*G01N 33/544* (2006.01)

(52) U.S. Cl.
CPC ........... *C07F 13/00* (2013.01); *G01N 33/544* (2013.01)

(58) Field of Classification Search
None
See application file for complete search history.

(56) References Cited

FOREIGN PATENT DOCUMENTS

EP 2 109 669 B1 1/2015

OTHER PUBLICATIONS

Siegmund et al. "Benzannulated Re(i)-NHC complexes: synthesis, photophysical properties and antimicrobial activity" Dalton Transactions, 2017, vol. 46, pp. 15269-15279.*
Cetinkaya et al., "Antimicrobial Activity of Carbene Complexes of Rhodium(I) and Ruthenium(II)", Arzneimittel-Forschung/Drug Research, 1996, 4 pages, vol. 46.
Chen et al., "Synthesis of N-heterocyclic carbene rhenium(I) carbonyl complexes", Dalton Transactions, 2012, pp. 2747-2754, vol. 41.
Hahn et al., "Template Synthesis of Benzannulated N-Heterocyclic Carbene Ligands", Chemistry—A European Journal, 2003, pp. 704-712, vol. 9, No. 3.
Kaloglu et al., "Synthesis and antimicrobial activity of bulky 3,5-di-tert-butyl substituent-containing silver-N-heterocyclic carbene complexes", Applied Organometallic Chemistry, 2017, 10 pages, vol. 31.
Lecina et al., "New rhenium complexes with ciprofloxacin as useful models for understanding the properties of [99mTc]-ciprofloxacin radiopharmaceutical", Bioorganic & Medicinal Chemistry, 2014, pp. 3262-3269, vol. 22.
Lo et al., "Design of Rhenium(I) Polypyridine Biotin Complexes as a New Class of Luminescent Probes for Avidin", Inorganic Chemistry, 2005, pp. 1992-2002, vol. 44, No. 6.
Siegmund, "Rhenium(I) N-Heterocyclic Carbene Complexes as Novel Organometallic Antibacterial Agents", 2017, 196 pages, Ruhr-Universität Bochum.
Search report issued for corresponding German patent application 10 2017 115 215.6 dated Mar. 12, 2018, 9 pages (for information purpose only).
Search report issued for corresponding International patent application PCT/EP2018/066100 dated Sep. 7, 2018, 8 pages (for information purpose only).
Oehninger et al., "N-Heterocyclic carbene metal complexes in medicinal chemistry", Dalton Transactions, 2013, pp. 3269-3284, vol. 42, The Royal Society of Chemistry.
Teyssot et al., "Metal-NHC complexes: a survey of anti-cancer properties", Dalton Transactions, 2009, 10 pages, The Royal Society of Chemistry.

(Continued)

*Primary Examiner* — Joseph R Kosack
(74) *Attorney, Agent, or Firm* — Viering Jentschura & Partner MBB

(57) ABSTRACT

A complex having the structure of formula (I)

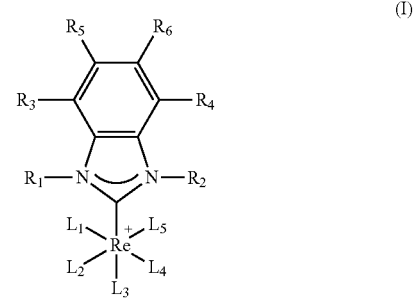

is disclosed. $L_1$, $L_2$, $L_3$, $L_4$, and $L_5$ may be or include independently metal-coordinating ligands selected from the group consisting of neutral ligands, anionic ligands, and mixed ligands, and combinations thereof. In a non-limiting embodiment, the complex is an N-heterocyclic carbene (NHC) Re(I) complex having an unsubstituted or substituted benzimidazol-2-ylidene ligand. The complex may be included in a pharmaceutical composition for treating gram (+) bacterial infections.

11 Claims, 8 Drawing Sheets

(56) References Cited

OTHER PUBLICATIONS

Hindi et al., "The Medicinal Applications of Imidazolium Carbene-Metal Complexes", Chemical Reviews, 2009, pp. 3859-3884, vol. 109, American Chemical Society.
Liu et al., "Synthesis of Cyclic Diamino-Substituted Metal Carbene Complexes", Organometallics, 1996, pp. 1055-1061, vol. 15, American Chemical Society.
Xue et al., "Spectroscopic and Excited-State Properties of Luminescent Rhenium(I) N-Heterocyclic Carbene Complexes Containing Aromatic Diimine Ligands", Organometallics, 1998, pp. 1622-1630, vol. 17, American Chemical Society.
Ng et al., "Synthesis, Characterization, and Photophysical Study of Luminescent Rhenium(I) Diimine Complexes with Various Types of N-Heterocyclic Carbene Ligands", Inorganic Chemistry, 2014, pp. 3022-3031, vol. 53, American Chemical Society.
Hiltner et al., "Synthesis and Characterization of Two New fac-Tricarbonylrhenium(I) Biscarbene Complexes", European Journal of Inorganic Chemistry, 2009, 22 pages, vol. 2009, Issue 13, John Wiley & Sons, Inc.
Huertos et al., "Effect of the Nature of the Substituent in N-Alkylimidazole Ligands on the Outcome of Deprotonation: Ring Opening versus the Formation of N-Heterocyclic Carbene Complexes", Chemistry—A European Journal, 2010, pp. 8495-8507, vol. 16, Wiley-VCH Verlag GmbH & Co. KGaA, Weinheim.
Blase et al., "Template synthesis of a macrocycle with a mixed NHC/phosphine donor set", Journal of Organometallic Chemistry, 2011, pp. 3337-3342, vol. 696, Elsevier B.V.
Martin et al., "Neutral and Cationic Mono- and Bis-N-heterocyclic Carbene Complexes Derived From Manganese and Rhenium Carbonyl Precursors", Organometallics, 2011, pp. 2200-2211, vol. 30, American Chemical Society.
Herrmann et al., "Einfache Synthese eines präparativ nützlichen Alkoxy(carbonyl)metallats", Chemische Berichte, 1992, pp. 1795-1799, including an English abstract on p. 1795, vol. 125, VCH Verlagsgesellschaft mbH, Weinheim.
Canella et al., "Synthesis and characterization of propylene and butylene bridged fac-tricarbonylrhenium(I) biscarbene complexes", Dalton Transactions, 2012, pp. 2110-2121, vol. 41, The Royal Society of Chemistry.
Hock et al., "Synthesis and characterisation of chelated cationic Re(CO)3bis(NHC)(WCA) complexes", Dalton Transactions, 2014, pp. 2259-2271, vol. 43, The Royal Society of Chemistry.
Chan et al., "Rhenium complexes of bidentate, bis-bidentate and tridentate N-heterocyclic carbene ligands", Dalton Transactions, 2015, pp. 19126-19140, vol. 44, The Royal Society of Chemistry.
Huckaba et al., "Photocatalytic Reduction of CO2 with Re-Pyridyl-NHCs", Inorganic Chemistry, 2016, pp. 682-690, vol. 55, American Chemical Society.
Casson et al., "N-Heterocyclic carbenes as π-acceptors in luminescent Re(I) triscarbonyl complexes", Dalton Transactions, 2011, pp. 11960-11967, vol. 40, The Royal Society of Chemistry.
Li et al., Blue-Green Luminescent Rhenium(I) Tricarbonyl Complexes with Pyridine-Functionalized N-Heterocyclic Carbene Ligands, Organometallics, 2012, pp. 3829-3835, vol. 31, American Chemical Society.
Hille et al., "Cationic rhenium complexes ligated with N-heterocyclic carbenes—an overview", Dalton Transactions, 2016, pp. 15-31, vol. 45, The Royal Society of Chemistry.
Hock et al., "Group 7 transition metal complexes with N-heterocyclic carbenes", Chemical Society Reviews, 2013, pp. 5073-5089, vol. 42, The Royal Society of Chemistry.
Leonidova et al., "Underestimated Potential of Organometallic Rhenium Complexes as Anticancer Agents", ACS Chemical Biology, 2014, pp. 2180-2193, vol. 9, American Chemical Society.
Lo et al., "Recent Exploitation of Luminescent Rhenium(I) Tricarbonyl Polypyridine Complexes as Biomolecular and Cellular Probes", European Journal of Inorganic Chemistry, 2011, pp. 3551-3568, Wiley-VCH Verlag GmbH & Co. KGaA, Weinheim.
Jürgens et al., "Rhenium and technetium based radiopharmaceuticals: Development and recent advances", Journal of Organometallic Chemistry, 2014, pp. 83-89, vol. 751, Elsevier B.V.
Wenzel et al., "Analysis of the Mechanism of Action of Potent Antibacterial Hetero-tri-organometallic Compounds: A Structurally New Class of Antibiotics", ACS Chemical Biology, 2013, pp. 1442-1450, vol. 8, American Chemical Society.
Patra et al., "Small organometallic compounds as antibacterial agents", Dalton Transactions, 2012, 10 pages, vol. 41, The Royal Society of Chemistry.

\* cited by examiner

Figure 6

| Complex | Solvent | Emission | | | Absorption |
|---|---|---|---|---|---|
| | | $\lambda_{max}$ [nm][a] | $\tau$ [ns][b] | $\Phi$[b] | $\lambda_{abs}$ [nm]/$\varepsilon$ [dm³ M⁻¹ cm⁻¹] |
| 4a | CH₃CN | 580 | 66 | 0.049 | 279 (31 400), 317 (11 480) 375 (2575) |
| | CH₃CN[c] | 580 | 120 | | |
| | H₂O | 581 | 45 | | |
| 5a | CH₃CN | 568 | 74 | 0.018 | 275 (52 640) 315 (29 530) 377 (13 130) |
| | CH₃CN[c] | 568 | 177 | | |
| | H₂O | 580 | 704 | | |
| 6a | CH₃CN | 568 | 123 | 0.025 | 275 (231 150) 385 (32 110) |
| | H₂O | 580 | 216 | | |
| 7a | CH₃CN | 580 | 224 | 0.023 | 285 (44 010) 385 (6815) |
| | H₂O | 583 | 480 | | | a) at 298 K; b) emission half-life and quantum yield are indicated with a statistical error of ± 15%; c) degassed.

| Complex | Gram-positive strains | | |
|---|---|---|---|
| | *B. subtilis* 168 DSM402 | *S. aureus* DSM 20231 | *S. aureus* ATCC 43300 (MRSA) |
| 3a | n.a. | n.a. | n.a. |
| 4a | 52 | 26 | 26 |
| 4b | 12,6 | 6,3 | 12,6 |
| 4c | 1,5 | 0,7 | 5,9 |
| 5a | 13 | 7 | 7 |
| 5b | 6,1 | 3 | 3 |
| 5c | 1,4 | 0,7 | 0,7 |
| 7a | 0,7-1,3 | 0,7 | 0,7 |
| 7b | 2,4 | 1,2 | 1,2 |
| 7c | 4,7 | 4,7 | 9,3 |

|  | Gram negative | | | Gram positive | | |
|---|---|---|---|---|---|---|
|  | E. coli | A. baumannii | P. aeruginosa | B. subtilis | S. aureus | S. aureus (MRSA) |
| DS50 | 788 | 394 | >788 | 6 | 6 | 6 |
| Biotin-DS50 | >531 | >531 | >531 | 33 | 33 | 17 |

EF-TU-BINDING METAL-CONTAINING ANTIBIOTIC

CROSS-REFERENCE TO RELATED APPLICATIONS

The present application is a national stage entry according to 35 U.S.C. § 371 of PCT application No.: PCT/EP2018/066100 filed on Jun. 18, 2018; which claims priority to German Patent Application Serial No.: 10 2017 115 215.6, which was filed on Jul. 7, 2017; both of which are incorporated herein by reference in their entirety and for all purposes.

TECHNICAL FIELD

The present invention is in the field of medicinal chemistry, and in particular relates to an N-heterocyclic carbene (NHC) Re(I) complexes.

BACKGROUND

Over the past decades, the rapid development of N-heterocyclic carbene (NHC) complexes with a broad spectrum of transition metals and ligand structures has led to fascinating insights and numerous applications, particularly in catalysis and photophysics.[1-3] A novel but rapidly evolving trend in organometallic chemistry is the use of metal carbene complexes for medical applications, particularly as therapeutic drugs. For example, NHC complexes of platinum, gold and silver have been found to offer promising antitumoral activity or even beneficial properties for the treatment of infectious diseases.[4-6]

Despite an increasing number of reports on Re(I) complexes with either monodentate[7-14] or multidentate[15-21] N-heterocyclic carbene ligands, very little is known about their biological properties and studies are focusing mainly on possible applications as OLEDs or catalysts.[22-23] This is particularly surprising since Re(I), with its structural diversity, its redox properties and the availability of radioactive analogues $^{186}$Re, $^{188}$Re and $^{99m}$Tc, offers enormous potential for diagnostic purposes or therapeutic drugs.[24-26] It is known that Re(I) complexes can exhibit antibacterial activity.[27] However, the already described antibacterial compounds are very large and consist of a peptide nucleic acid scaffold with an alkyne side chain substituted with a cymantrene, a (dipicolyl)Re(CO)$_3$ unit and either a ferrocene (FcPNA) or a ruthenocene (RcPNA). For medical use, a molecule with a lower molecular weight would be desirable.

Furthermore, due to ever-increasing bacterial resistances, there is an urgent need to find novel antibiotic lead structures.

Therefore, there is currently a need for a reliable antibiotic with a novel lead structure that has not yet been used against bacterial infections.

SUMMARY

The inventors have surprisingly found in test series that an N-heterocyclic carbene (NHC) Re(I) complex with an unsubstituted or substituted benzimidazol-2-ylidene ligand, as described herein, has a high antimicrobial effect against Gram-positive bacteria. Furthermore, it was found that the complexes described herein have a different mode of action compared to other antibiotics targeting the same target, such as nocathiacin I, GE2270 A and kirromycin. These properties allow for the use of structurally and mechanistically new antibiotics and increase the probability that the development of resistances to the complexes will be very delayed.

In a first aspect, a complex may have the structure of formula (I)

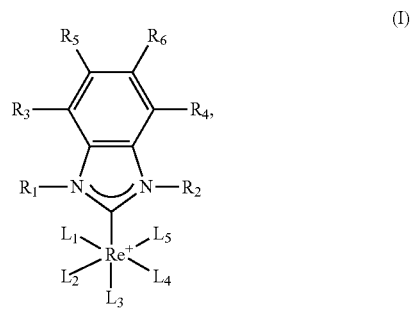

wherein
$R_1$, $R_2$, $R_3$, $R_4$, $R_5$, and $R_6$ are independently selected from the group consisting of H, linear or branched, substituted or unsubstituted alkyl, linear or branched, substituted or unsubstituted heteroalkyl, linear or branched, substituted or unsubstituted alkenyl, linear or branched, substituted or unsubstituted heteroalkenyl, linear or branched, substituted or unsubstituted alkynyl, linear or branched, substituted or unsubstituted heteroalkynyl, substituted or unsubstituted cycloalkyl, substituted or unsubstituted heterocycloalkyl, substituted or unsubstituted aryl, substituted or unsubstituted heteroaryl, linear or branched, substituted or unsubstituted alkylaryl, linear or branched, substituted or unsubstituted heteroalkylaryl, wherein each of these groups have up to 20 carbon atoms; and $L_1$, $L_2$, $L_3$, $L_4$, and $L_5$ are independently metal-coordinating ligands selected from the group consisting of neutral ligands, anionic ligands and mixed ligands.

In various embodiments, a) $L_1$, $L_2$, $L_3$, $L_4$ and $L_5$ are independently selected from the group consisting of halo, carbonyl, $C_1$-$C_{10}$ alkyl, $C_1$-$C_{10}$ alkoxy, sulfide, thiocyanate, nitrate, azide, fluoride, hydroxide ion, $H_2O$, nitrite, isothiocyanate, acetonitrile, pyridine, ammonia, triphenylphosphine, cyanide, carbon monoxide, linear or branched, substituted or unsubstituted alkene having up to 20 carbon atoms, benzene, cyclopentadienyl, nitrosyl, oxoligand, sulfites, tricyclohexylphosphane, trimethylphosphane, tri(o-tolyl)phosphane, cycloheptatriene, carbon dioxide; or b) two or three of $L_1$, $L_2$, $L_3$, $L_4$, and $L_5$ are linked to form a molecule selected from the group consisting of oxalate, ethylenediamine, 2,2' bipyridine, 1,10-phenanthroline, acetylacetonate, aminopolycarboxylic acids, 1,2-bis(diphenylphosphino)ethane, 1,1-bis(diphenylphosphino)methane, diethylenetriamine, dimethylglyoximate, glycine, iminodiacetic acid, nitrilotriacetic acid, pyrazine, scorpion ligands, 2,2';6',2"-terpyridine, triazacyclononane, di-(2-picolyl)amine, 2,2'-dipyridylamine, tris(2-pyridylmethyl)amine, N,N,N',N'-tetramethylethyleneediamine (TMEDA), N-propyl (2-pyridyl)methanimine (NPrPMI),

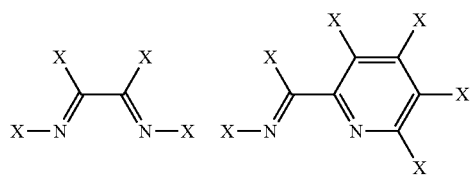

-continued

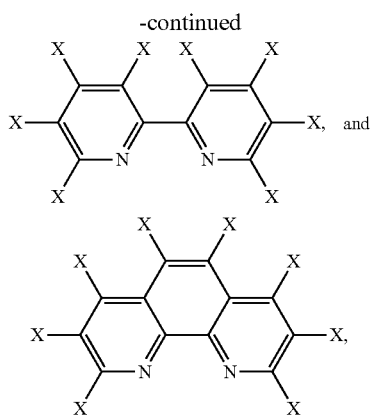

wherein each X is independently H or a linear or branched alkyl having up to 20 carbon atoms; and wherein $L_1$, $L_2$, $L_3$, $L_4$, and $L_5$, which are not linked to other metal-coordinating ligands, are as defined in a).

In various embodiments, $L_4$ and $L_5$ are linked to form a molecule and are selected from the group consisting of

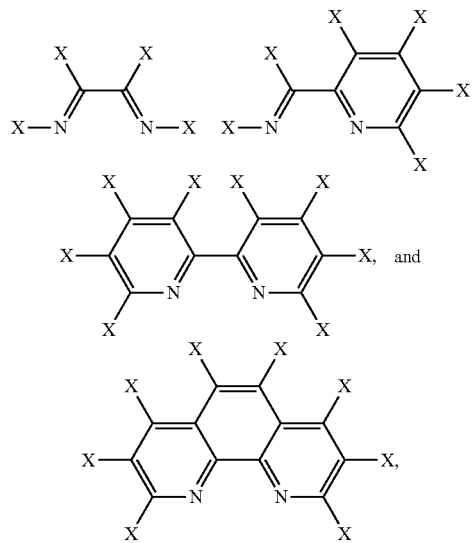

wherein each X is independently H or a linear or branched alkyl having up to 20 carbon atoms.

In various embodiments, $L_4$ and $L_5$ are selected from the group consisting of

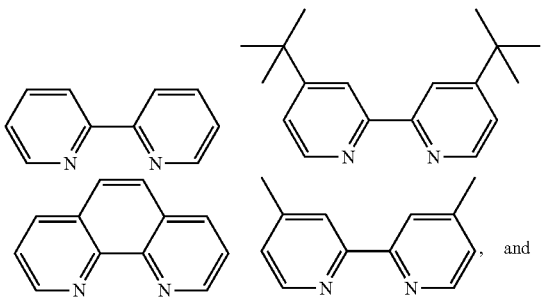

-continued

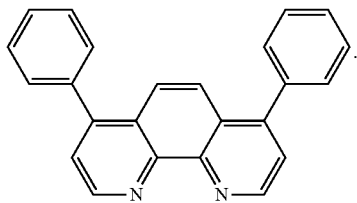

In various embodiments, $R_1$ is H, $CH_2$-phenyl, or

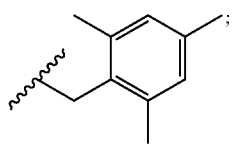 [SMILES: *Cc1c(C)cc(C)cc1C]

and/or $R_2$ is H.

In various embodiments, $R_3$-$R_6$ are H; and/or $L_1$-$L_3$ are CO.

In various embodiments, the complex may include the following:

a) $R_1$ is H, $CH_2$-phenyl or

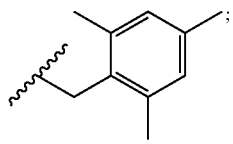 [SMILES: *Cc1c(C)cc(C)cc1C]

and $R_2$ is H; and $R_3$-$R_6$ are H; and $L_1$-$L_3$ are CO; and $L_4$ and $L_5$ are linked to form

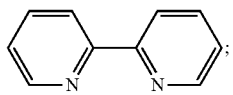 [SMILES: c1ccc(-c2ccccn2)nc1]

or b) $R_1$ is H, $CH_2$-phenyl or

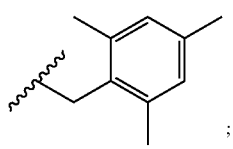 [SMILES: *Cc1c(C)cc(C)cc1C]

and

R$_2$ is H; and

R$_3$-R$_6$ are H; and

L$_1$-L$_3$ are CO; and

L$_4$ and L$_5$ are linked to form

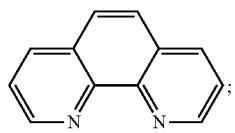

or c) R$_1$ is H; and

R$_2$ is H; and

R$_3$-R$_6$ are H; and

L$_1$-L$_3$ are CO; and

L$_4$ and L$_5$ are linked to form

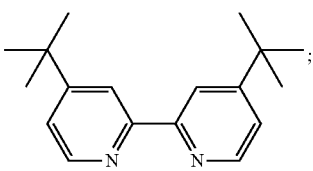 [SMILES: CC(C)(C)c1ccnc(-c2cc(C(C)(C)C)ccn2)c1]

or d) R$_1$ is H, CH$_2$-phenyl or

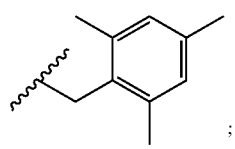 [SMILES: *Cc1c(C)cc(C)cc1C]

and

R$_2$ is H; and

R$_3$-R$_6$ are H; and

L$_1$-L$_3$ are CO; and

L$_4$ and L$_5$ are linked to form

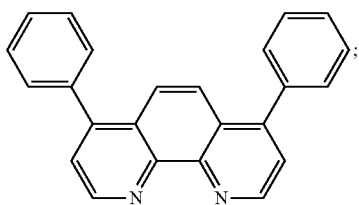 [SMILES: c1ccc(-c2ccnc3c2ccc2c(-c4ccccc4)ccnc23)cc1]

or e) R$_1$ is H; and

R$_2$ is H; and

R$_3$-R$_6$ are H; and

L$_1$-L$_3$ are CO; and

L$_4$ and L$_5$ are linked to form

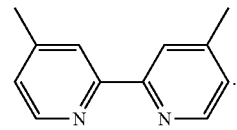

A second aspect is directed to a pharmaceutical composition comprising an inventive and a pharmaceutically acceptable carrier or excipient.

In a third aspect, the complex may be used as a medicament.

A fourth aspect is directed to an inventive complex for use in the treatment of a bacterial infection or bacterial infestation, wherein the bacterial infection or bacterial infestation is caused by a Gram-positive bacterium.

In various embodiments, the Gram-positive bacterium is selected from the group consisting of *Bacillus* or *Staphylococcus*.

In a further aspect, a method for the preparation of a complex having the structure of formula (II) may include

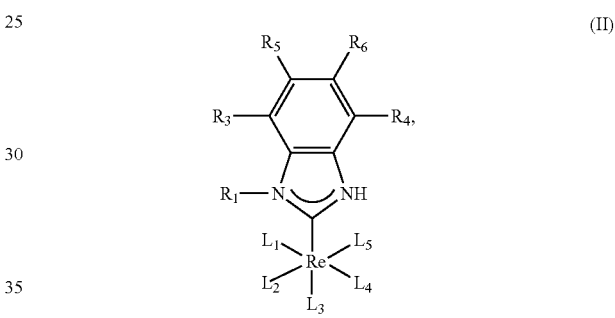

wherein

R$_1$, R$_3$, R$_4$, R$_5$ and R$_6$ are independently selected from the group consisting of H, linear or branched, substituted or unsubstituted alkyl, linear or branched, substituted or unsubstituted heteroalkyl, linear or branched, substituted or unsubstituted alkenyl, linear or branched, substituted or unsubstituted heteroalkenyl, linear or branched, substituted or unsubstituted alkynyl, substituted or unsubstituted heteroalkynyl, substituted or unsubstituted cycloalkyl, substituted or unsubstituted heterocycloalkyl, substituted or unsubstituted aryl, substituted or unsubstituted heteroaryl, linear or branched, substituted or unsubstituted alkylaryl, linear or branched, substituted or unsubstituted heteroalkylaryl, each of these groups having up to 20 carbon atoms; and L$_1$, L$_2$, L$_3$, L$_4$ and L$_5$ are independently metal-coordinating ligands selected from the group consisting of neutral ligands, anionic ligands and mixed ligands;

comprising contacting a compound having the structure of formula (III)

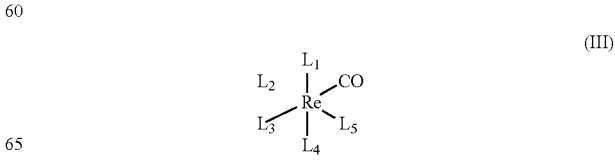

with a compound having the structure of formula (IV)

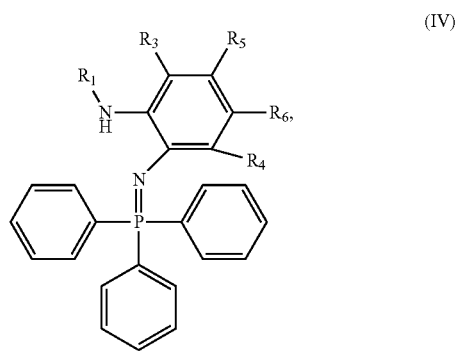

to form the complex having the structure of formula (II).

A sixth aspect is directed to a method for identifying a molecule, which interacts with a complex, comprising a) providing a complex, wherein $R_5$ is a linker group; and b) immobilizing the complex of a) on a solid support, wherein the solid support binds the complex via the linker group;

c) contacting the immobilized complex with a solution comprising the molecules of interest; and (d) releasing the molecules interacting with the immobilized complex and identifying those molecules.

In different embodiments, the linker group is

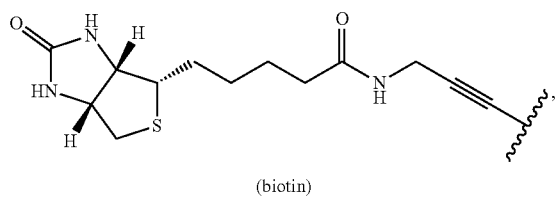 [SMILES: *C#CCNC(=O)CCCC[C@@H]1SC[C@@H]2NC(=O)N[C@@H]21]

(biotin)

and the solid carrier comprises avidin and/or streptavidin.

BRIEF DESCRIPTION OF THE DRAWINGS

The complex is explained in more detail below using several illustrations. These illustrations support the teachings explained in the description, but do not restrict them. Here shows:

FIG. 2: Possible mechanism of formation of the Re(I) carbene complex 3a.

FIG. 6: Summary of the photophysical properties of complexes 4a-7a.

DETAILED DESCRIPTION

Figure 1:
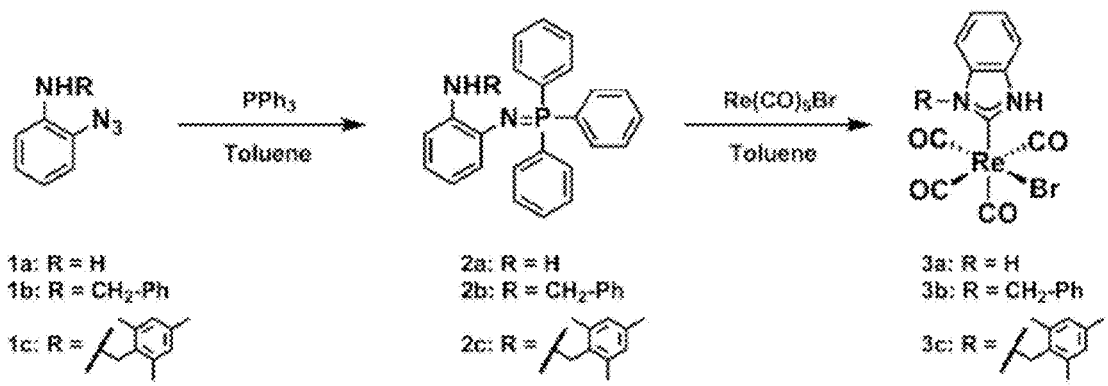
FIG. 1: Scheme of the preparation of the neutral benzimidazol-2-ylidene complexes 3a-3c.

The inventors have surprisingly found structurally and mechanistically new antibiotics that allow for the selective treatment of Gram-positive bacteria.

Therefore, in a first aspect, a complex may have the structure of formula (I)

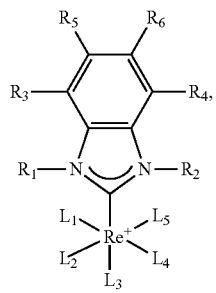

(II)

wherein $R_1$, $R_2$, $R_3$, $R_4$, $R_5$, and $R_6$ are independently selected from the group consisting of H, linear or branched, substituted or unsubstituted alkyl, linear or branched, substituted or unsubstituted heteroalkyl, linear or branched, substituted or unsubstituted alkenyl, linear or branched, substituted or unsubstituted heteroalkenyl, linear or branched, substituted or unsubstituted alkynyl, linear or branched, substituted or unsubstituted heteroalkynyl, substituted or unsubstituted cycloalkyl, substituted or unsubstituted heterocycloalkyl, substituted or unsubstituted aryl, substituted or unsubstituted heteroaryl, linear or branched, substituted or unsubstituted alkylaryl, linear or branched, substituted or unsubstituted heteroalkylaryl, each of these groups having up to 20 carbon atoms; and $L_1$, $L_2$, $L_3$, $L_4$, and $L_5$ are independently metal-coordinating ligands selected from the group consisting of neutral ligands, anionic ligands and mixed ligands.

The term "rhenium" or "Re", as herein used interchangeably, means a chemical element with an atomic number of 75. In the periodic table of the elements, rhenium is in the 7th subgroup (group 7) or manganese group. It is a very rare, silver-white shiny, heavy transition metal.

The term "alkyl", alone or as part of another substituent, refers to, unless stated otherwise, a linear (i.e. unbranched) or branched chain or a combination thereof, which is completely saturated and may include di- and polyvalent radicals. Alkyls are more specifically defined by the number of carbon atoms they contain (e.g. $C_1$-$C_{10}$ means one to ten carbons). Alkyls with up to 20, up to 15, up to 10 or up to 5 carbon atoms may be used. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl) methyl, cyclopropylmethyl, homologues and isomers of, for example, n-pentyl, n-hexyl, n-heptyl, n-octyl and the like.

The term "alkylene", alone or as part of another substituent, refers to a divalent radical derived from an alkyl as exemplified but not limited to —CH$_2$CH$_2$CH$_2$CH$_2$—. Typically, an alkyl (or alkylene) group will have 1 to 24 carbon atoms, such as having 10 or less carbon atoms. A "lower alkyl" or "lower alkylene" is a shorter alkyl or alkylene group generally having eight or fewer carbon atoms.

The term "heteroalkyl", alone or in combination with another term, denotes, unless stated otherwise, a stable linear or branched or cyclic hydrocarbon radical or combinations thereof consisting of at least one carbon atom and at least one heteroatom selected from the group consisting of O, N, P, Si and S, and wherein the nitrogen and sulfur atoms can optionally be oxidized and the nitrogen heteroatom can optionally be quaternized. The heteroatom(s) O, N, P and S and Si may be placed at any inner position of the heteroalkyl group or at the position where the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)$_2$, —CH$_2$—S—CH$_2$—CH$_3$, —CH$_2$—CH$_2$, —SCHO—CH$_2$—S(O)$_2$—CH$_3$, —CH═CH—O—CH$_3$, —Si(CH$_3$)$_3$, —CH$_2$—CH═N—OCH$_3$, —CH═CH—N(CH$_3$)$_2$, O—CH$_3$, —O—CH$_2$—CH$_3$ and —CN. Up to two heteroatoms can be consecutive, such as —CH$_2$—NH—OCH$_3$ and —CH$_2$—O—Si(CH$_3$)$_3$. Similarly, the term "heteroalkylene", alone or as part of another substituent, refers to a divalent radical derived from heteroalkyl as exemplified, but not limited to, —CH$_2$—CH$_2$—CH—CH$_2$—CH$_2$— and —CH$_2$—S—CH$_2$—CH$_2$—NH—CH$_2$—. For heteroalkylene groups, heteroatoms may also occupy one or both of the chain termini (e.g. alkyleneoxy, alkylenedioxy, alkyleneamino, alkylenediamino and the like). Furthermore, for alkylene and heteroalkylene linking groups, no orientation of the linking group is given by the direction, in which the formula of the linking group is written. For example, the formula —C(O)$_2$R'— means both —C(O)$_2$R'— and —R'C(O)$_2$—. As described above, heteroalkyl groups as used herein include those groups, which attach to the remainder of the molecule through a heteroatom such as —C(O)R', —C(O)NR', —NR'R", —OR', —SR and/or —SO$_2$R'. When "heteroalkyl" is recited followed by recitations of specific heteroalkyl groups such as —NR'R" or the like, it is understood that the terms heteroalkyl and —NR'R" are not redundant or mutually exclusive. Rather, the specific heteroalkyl groups are cited for clarity. The term "heteroalkyl" should therefore not be interpreted herein as specific exclusive heteroalkyl groups, such as —NR'R" or the like.

The terms "cycloalkyl" and "heterocycloalkyl", taken together or in combination with other terms, represent cyclic versions of "alkyl" and "heteroalkyl", unless otherwise indicated. In addition, in the case of heterocycloalkyl, a heteroatom may occupy the position where the heterocycle is attached to the remainder of the molecule. Examples of cycloalkyl comprise, but are not limited to, cyclopentyl, cyclohexyl, 1-cyclohexenyl, 3-cyclohexenyl, cycloheptyl and the like. Examples of heterocycloalkyl comprise, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl and the like. "Cycloalkylene" and "heterocycloalkylene" refers to a divalent radical derived from cycloalkyl and heterocycloalkyl, respectively.

The terms "halogen" or "halo", alone or as part of another substituent, refer to, unless stated otherwise, a fluorine, chlorine, bromine or iodine atom. In addition, terms such as "haloalkyl" shall include monohaloalkyl and polyhaloalkyl. For example, the term "halo($C_1$-$C_4$)alkyl" refers to, but is not limited to, trifluoromethyl, 2,2,2-trifluoroethyl, 4-chlorobutyl, 3-bromopropyl and the like.

The term "aryl" refers to, unless stated otherwise, a polyunsaturated aromatic hydrocarbon substituent, which may be a single ring or a plurality of rings (such as 1 to 3 rings) fused or covalently linked together. The term "heteroaryl" refers to aryl groups (or rings) containing one to four heteroatoms selected from N, O and S, wherein the nitrogen and sulfur atoms are optionally oxidized and the nitrogen atom(s) are optionally quaternized. A heteroaryl group may be attached to the remainder of the molecule by a carbon or heteroatom. Non-restrictive examples of aryl and heteroaryl groups comprise phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-Isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the aryl and heteroaryl ring systems mentioned above are selected from the group of acceptable substituents described below. "Arylene" and "heteroarylene" refers to a divalent radical derived from an aryl and heteroaryl.

The term "arylalkyl" is intended to include those radicals, in which an aryl group is attached to an alkyl group (e.g. benzyl, phenethyl, pyridylmethyl and the like). The term "heteroarylalkyl" includes the above-described groups, wherein one or more carbon atoms of the alkyl or aryl moiety (e.g. a methylene group) are substituted for example by an oxygen atom (e.g. phenoxymethyl, 2-pyridyloxymethyl, 3-(1-naphthyloxy)propyl and the like).

When a heteroalkyl, heterocycloalkyl or heteroaryl contains a certain number of members (e.g. "3 to 7 members"), the term "member" refers to a carbon or heteroatom.

The term "oxo", as used herein, refers to an oxygen atom that is doubly bonded to a carbon atom.

Each of the above terms (e.g. "alkyl", "heteroalkyl", "aryl" and "heteroaryl") is intended to include both substituted and unsubstituted forms of the given radical. Non-limiting substituents for each type of radical are given below.

Substituents for the alkyl, heteroalkyl, alkylene, alkenyl, heteroalkylene, heteroalkenyl, alkynyl, cycloalkyl, heterocycloalkyl, cycloalkenyl and heterocycloalkenyl radicals may be one or more of a plurality of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NRR", —NR"C(O)R', —S(O)R', —S(O)R', —S—(O)R', —S—(O)R', —S—(O)$_2$R', —S(O)$_2$NR'R", —NRSO$_2$R', —CN and —NO$_2$ in an amount from zero to (2 m'+1), wherein m' is the total number of carbon atoms in the radical. R', R" and R'" are each independently hydrogen, substituted or unsubstituted heteroalkyl, substituted or unsubstituted cycloalkyl, substituted or unsubstituted heterocycloalkyl, substituted or unsubstituted aryl (e.g. aryl substituted with 1-3 halogens), substituted or unsubstituted alkyl, alkoxy or thioalkoxy groups, or arylalkyl groups. For example, if a compound contains more than one R group, each of the R groups is independently selected from e.g. R', R", R'" and R"" groups, respectively. When R' and R" are bonded to the same nitrogen atom, they can be combined with the nitrogen atom to form a 4-, 5-, 6- or 7-membered ring. For example, —NR'R" shall include, but not be limited to, 1-pyrrolidinyl and 4-morpholinyl. From the above discussion of substituents, the expert will understand that the term "alkyl" shall include groups that include carbon groups bound to groups other than hydrogen groups, such as haloalkyl (e.g. —CF$_3$ and —CH$_2$CF$_3$) and acyl (e.g. —C(O)CH$_3$, —C(O)CF$_3$, —C(O)CH$_2$OCH$_3$ and the like).

Similar to the substituents described for the alkyl radical, the substituents for the aryl and heteroaryl groups may vary and are selected, for example, from halogen, —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl in a number from zero to the total number of open valencies in the aromatic ring system; and wherein R', R", R'" and R"" are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. For example, if a compound contains more than one group R, each of the R groups is independently selected from e.g. R', R", R'" and R"" groups, respectively.

Furthermore, in non-limiting embodiments, two substituents on adjacent ring atoms may be combined to form a cyclic group, which may be saturated, unsaturated or aromatic and is selected from aryl, heteroaryl, cycloalkyl, cycloheteroalkyl, all of which may be substituted as defined above for the respective groups.

As used herein, the term "heteroatom" or "ring heteroatom" refers to oxygen (O), nitrogen (N), sulphur (S), phosphorus (P) and silicon (Si).

The term "alkenyl", as used herein, is a hydrocarbon group having 2 to 20 carbon atoms with a structural formula containing at least one carbon-carbon double bond. Asymmetric structures such as (A1A2)C=C(A3A4) shall include both E- and Z-isomers. The alkenyl group may be substituted with one or more groups including, but not limited to, alkyl, cycloalkyl, alkoxy, alkenyl, cycloalkenyl, alkynyl, aryl, heteroaryl, aldehyde, amino, carboxylic acid, ester, ether, halide, hydroxy, ketone, azide, nitro, silyl, sulfoxo or thiol as described herein.

The term "cycloalkenyl" as used herein is a non-aromatic carbon-based ring composed of at least three carbon atoms and containing at least one carbon-carbon double bond, i.e. C=C. Examples of cycloalkenyl groups include, but are not limited to, cyclopropenyl, cyclobutenyl, cyclopentenyl, cyclopentadienyl, cyclohexenyl, cyclohexadienyl, norbornenyl and the like. The cycloalkenyl group may be substituted or unsubstituted. The cycloalkenyl group may be substituted with one or more groups including, but not limited to, alkyl, cycloalkyl, alkoxy, alkenyl, cycloalkenyl, alkynyl, aryl, heteroaryl, aldehyde, amino, carboxylic acid, ester, ether, halide, hydroxy, ketone, azide, nitro, silyl, sulfoxo or thiol, as described herein.

The term "alkynyl", as used herein, is a hydrocarbon group having 2 to 20 carbon atoms with a structural formula containing at least one carbon-carbon triple bond. The alkynyl group may be unsubstituted or substituted with one or more groups including, but not limited to, alkyl, cycloalkyl, alkoxy, alkenyl, cycloalkenyl, alkynyl, aryl, heteroaryl, aldehyde, amino, carboxylic acid, ester, ether, halide, hydroxy, ketone, azide, nitro, silyl, sulfoxo or thiol, as described herein.

The term "ligand" or "metal-coordinating ligand", as interchangeably used herein, is an atom or molecule, which can bind ("coordinate") to a central metal ion via a coordinate bond (obsolete also "dative bond"). The coordinative bond is formed due to the Lewis character of the binding partners involved: ligands are Lewis bases (electron pair donors), metal ions are Lewis acids (electron pair acceptors). Ligands are classified according to their charge: negatively charged ligands are abbreviated as X-type or anionic ligands (e.g. halides), while neutral ligands are abbreviated as L-type (e.g. phosphanes). Ligands containing both a negative charged part and a neutral part are referred to as mixed ligands or mixed charged ligands. The denticity indicates how many bonds to the central atom a ligand can form. Ligands that form only one bond to the central atom are called monodentate. Ammonia ($NH_3$, in the complex called amine) is for example a monodentate ligand: $H_3N-M$. If a ligand has several coordination sites, which can also be used simultaneously for coordination at the same metal centre, this is referred to as a chelate ligand (Greek chelé=pincers). In formulas (I) and (II) shown herein, $L_1$, $L_2$, $L_3$, $L_4$, and $L_5$ are each to be understood as one ligand. The coordination environment of the rhenium atom in the complexes can be varied by different combinations of monodentate ligands and/or chelating ligands. The following ligand combinations are possible without being limited thereto: five monodentate ligands; one bidentate ligand and three monodentate ligands; one tridentate ligand and two monodentate ligands; one tetradentate ligand and one monodentate ligand; one pentadentate ligand; one bidentate ligand and one tridentate ligand; and two bidentate ligand and one monodentate ligand. The combination of a bidentate ligand and three monodentate ligands may be included in the complex in a non-limiting embodiment.

In various embodiments, a) $L_1$, $L_2$, $L_3$, $L_4$, and $L_5$ are independently selected from the group consisting of halo, carbonyl, $C_1$-$C_{10}$ alkyl, $C_1$-$C_{10}$ alkoxy, sulfide, thiocyanate, nitrate, azide, fluoride, hydroxide ion, $H_2O$, nitrite, isothiocyanate, acetonitrile, pyridine, ammonia, triphenylphosphine, cyanide, carbon monoxide, linear or branched, substituted or unsubstituted alkene having up to 20 carbon atoms, benzene, cyclopentadienyl, nitrosyl, oxoligand, sulfites, tricyclohexylphosphane, trimethylphosphane, tri(o-tolyl)phosphane, cycloheptatriene, carbon dioxide; or b) two or three of $L_1$, $L_2$, $L_3$, $L_4$, and $L_5$ are linked to form a molecule selected from the group consisting of oxalate, ethylenediamine, 2,2' bipyridine, 1,10-phenanthroline, acetylacetonate, aminopolycarboxylic acids, 1,2-bis(diphenylphosphino)ethane, 1,1-bis(diphenylphosphino)methane, diethylenetriamine, dimethylglyoximate, glycine, iminodiacetic acid, nitrilotriacetic acid, pyrazine, scorpion ligands, 2,2';6',2"-terpyridine, triazacyclononane, di-(2-picolyl) amine, 2,2'-dipyridylamine, tris(2-pyridylmethyl)amine, N,N,N',N'-tetramethylethyleneediamine (TMEDA), N-propyl(2-pyridyl)methanimine (NPrPMI),

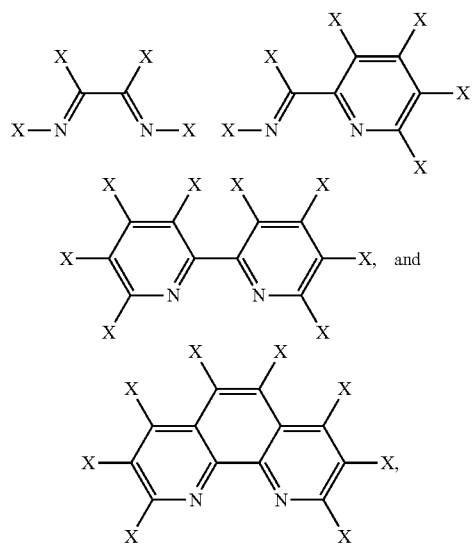

wherein each X is independently H or a linear or branched alkyl having up to 20 carbon atoms; and wherein $L_1$, $L_2$, $L_3$, $L_4$ and $L_5$, which are not linked to other metal-coordinating ligands, are as defined in a).

The term "linked to form a molecule", as used herein, denotes the compound that provides at least two of the five ligands at the coordinated rhenium atom. In a non-limiting embodiment, these linked ligands are indirectly connected by one or more atoms, all of which are linked by covalent bonds to form a molecule. In particular, two ligands may be tertiary nitrogen atoms, each linked to the carbon atoms $C_x$ and $C_y$ by double bonds, wherein $C_x$ and $C_y$ are linked directly by a single bond. Furthermore, the atoms $C_x$ and $C_y$ can be part of an aryl system described above.

In various embodiments, $L_4$ and $L_5$ are linked to form a molecule and are selected from the group consisting of

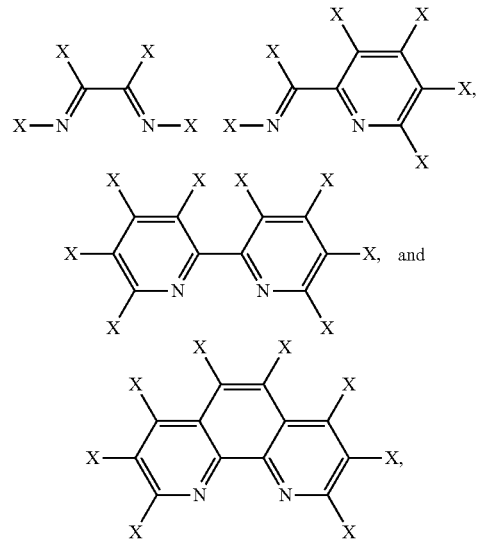

wherein each X is independently H or a linear or branched alkyl having up to 20 carbon atoms.

In various embodiments, $L_4$ and $L_5$ are selected from the group consisting of

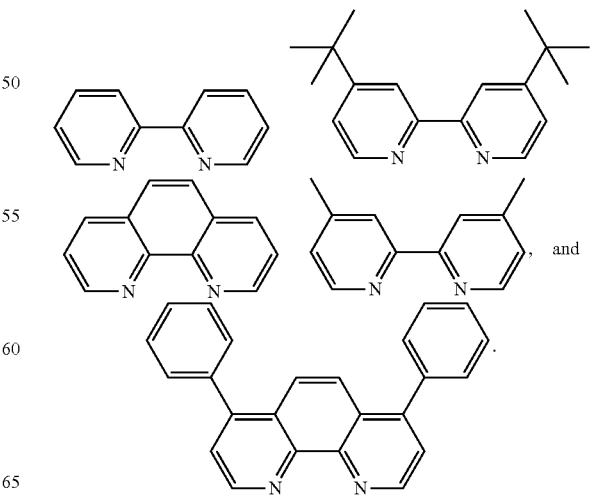

In various embodiments, $R_1$ is H, $CH_2$-phenyl, or

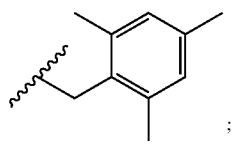 [SMILES: *Cc1c(C)cc(C)cc1C]

and/or
$R_2$ is H.

In various embodiments, $R_3$-$R_6$ are H; and/or $L_1$-$L_3$ are CO.

In various embodiments, the complex may include the following:

a) $R_1$ is H, $CH_2$-phenyl or

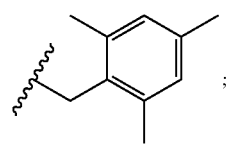 [SMILES: *Cc1c(C)cc(C)cc1C]

and
$R_2$ is H; and
$R_3$-$R_6$ are H; and
$L_1$-$L_3$ are CO; and
$L_4$ and $L_5$ are linked to form

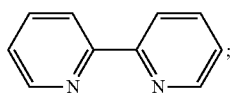 [SMILES: c1ccc(-c2ccccn2)nc1]

or
b) $R_1$ is H, $CH_2$-phenyl or

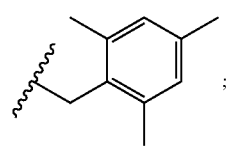 [SMILES: *Cc1c(C)cc(C)cc1C]

and
$R_2$ is H; and
$R_3$-$R_6$ are H; and
$L_1$-$L_3$ are CO; and
$L_4$ and $L_5$ are linked to form

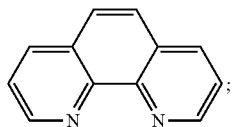

or
c) $R_1$ is H; and
$R_2$ is H; and
$R_3$-$R_6$ are H; and
$L_1$-$L_3$ are CO; and
$L_4$ and $L_5$ are linked to form

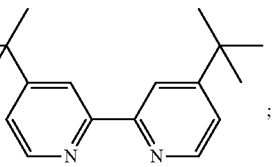

or
d) $R_1$ is H, $CH_2$-phenyl or

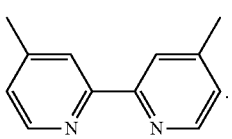

and
$R_2$ is H; and
$R_3$-$R_6$ are H; and
$L_1$-$L_3$ are CO; and
$L_4$ and $L_5$ are linked to form

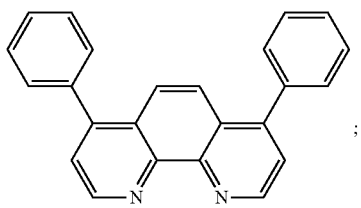

or
e) $R_1$ is H; and
$R_2$ is H; and
$R_3$-$R_6$ are H; and
$L_1$-$L_3$ are CO; and
$L_4$ and $L_5$ are linked to form A second aspect is directed to a pharmaceutical composition comprising an inventive and a pharmaceutically acceptable carrier or excipient.

A "pharmaceutical composition" refers to a mixture of one or more of the compounds described herein or physiologically/pharmaceutically acceptable salts or prodrugs thereof with other chemical components, such as physiologically/pharmaceutically acceptable carriers and excipients/adjuvants. The purpose of a pharmaceutical composition is to facilitate the administration of a compound to an organism.

As used herein, a "physiologically/pharmaceutically acceptable carrier" refers to a carrier or diluent that does not cause significant irritation to an organism and does not reverse the biological activity and properties of the compound administered.

A "pharmaceutically acceptable excipient/adjuvant" refers to an inert substance added to a pharmaceutical composition to further facilitate the administration of a compound. Examples, without restriction, include calcium carbonate, calcium phosphate, various sugars and types of starch, cellulose derivatives, gelatin, vegetable oils and polyethylene glycols.

As used herein, the term "pharmaceutically acceptable salt" refers to those salts that maintain the biological activity and properties of the initial compound. Such salts include, but are not limited to: (1) an acid addition salt obtained by reacting the free base of the starting compound with inorganic acids such as hydrochloric acid, hydrobromic acid, nitric acid, phosphoric acid, sulphuric acid and perchloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like, such as hydrochloric acid or (L)-lactic acid; or (2) salts that are formed when an acid proton present in the starting compound is either replaced by a metal ion, such as an alkali metal ion, such as sodium or potassium, an alkaline earth metal, such as magnesium or calcium, or an aluminium ion, or (3) coordinated with an organic base such as ethanolamine, diethanolamine, triethanolamine, tromethamine, N-methylglucamine and the like.

Additionally, it is contemplated that compounds are metabolized by enzymes in the body of the organism, such as a human, to produce a metabolite that has the desired functionality. Such metabolites are within the scope.

"Treatment" and "treat" refer to a method of alleviating or eliminating a disease or disorder and/or its associated symptoms.

"Organism" refers to any living being consisting of at least one cell. A living organism can be as simple as a single eukaryotic cell or as complex as a mammal, including a human.

"Therapeutically effective amount" refers to the amount of compound administered, which, to some extent, will relieve one or more of the symptoms of the disorder to be treated.

In a third aspect, the complex may be used as a medicament.

The term "medicament" or "drug" as used herein interchangeably shall include any substance (i.e. a compound or composition of matter), which, when administered to an organism (human or animal), has a desired pharmacological and/or physiological effect by local injection and/or systemic action. The term therefore includes substances traditionally considered as active substances, drugs and bioactive agents as well as biopharmaceuticals (e.g. peptides, hormones, nucleic acids, gene constructs, etc.) typically used to treat a number of conditions that are broadly defined as diseases, disorders, infections and the like.

Pharmaceutical forms of administration, quantities of substances used to treat the diseases and symptoms described herein as well as the time intervals between applications are known in the state of the art. In this respect, reference is made to European Patent EP2226329 B1, and in particular to the section "Administration and Pharmaceutical Composition" (paragraphs [0044]-[0080]), which is hereby expressly included by reference in the present description.

A fourth aspect is directed to the complex for use in the treatment of a bacterial infection or bacterial infestation, wherein the bacterial infection or bacterial infestation is caused by a Gram-positive bacterium.

The term "infection" or "bacterial infection", as used herein, refers to the presence of bacteria in or on a subject, whose inhibition would lead to a benefit for the subject. As such, in addition to referring to the presence of bacteria, the term "infection" also refers to the normal bacterial flora whose inhibition is undesirable. The term "infection" or "bacterial infection" also includes infections caused by Gram-positive and Gram-negative bacteria. An infection can also be understood as an accumulation of bacteria in a subject, where such an accumulation of bacteria is not present in a healthy reference subject or is present in a significantly reduced amount.

The term "bacterial infestation", as used herein, refers to an accumulation of bacteria on or in the body of a subject without directly altering the tissue or body part, on or in which the bacterial accumulation is located, or allowing the bacteria to enter that tissue or body part. Such tissue or part of the body, for example, may be hair, skin or teeth.

In different embodiments, the Gram-positive bacterium is selected from the group consisting of *Bacillus* or *Staphylococcus*.

"Gram-positive bacteria", or also "Firmicutes", "genuine bacteria" (Bacteria, Eubacteria), are bacteria, which have a Gram-positive cell wall (bacterial cell wall, Gram staining) or are related to each other as determined by molecular genetic examinations (16S-rRNA). Phylogenetically, 2 main lineages can be distinguished: 1) the forms with low G+C content in the DNA (*Bacillus/Clostridium* group with the subgroups: *Bacillus/Lactobacillus/Streptococcus*, *Heliobacterium*, *Mollicutes* (bacteria not having a cell wall, and related ones) as well as the *Synthrophomonas/Thermoanaerobacter* lineage and 2) the forms with high G+C content. In the first main lineage, most unicellular, coccoidal, cell wall-less bacteria are classified as well as the non-spore-forming rod-shaped species and the spore-forming species (*Clostridiaceae*). The 2nd main lineage includes actinomycetes and related organisms, including coryneform bacteria, mycobacteria and nocardias. Gram-positive bacteria comprise, but are not limited to, the following classes: *Staphylococci*, *Streptococci*, *Pneumococci*, *Enterococci*, *Bacilli*, *Clostridia*, *Corynebacterium*, *Listeria* and *Actinomyces*.

In a further aspect, a method for the preparation of a complex may have the structure of formula (II)

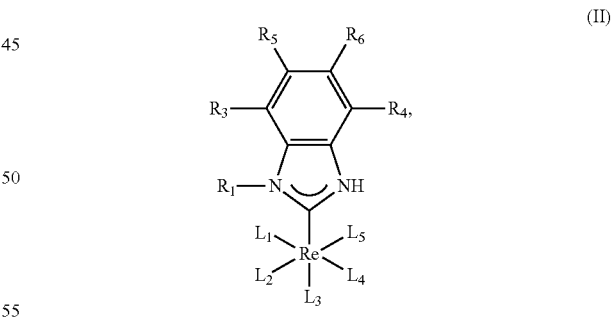

wherein
$R_1$, $R_3$, $R_4$, $R_5$, and $R_6$ are independently selected from the group consisting of H, linear or branched, substituted or unsubstituted alkyl, linear or branched, substituted or unsubstituted heteroalkyl, linear or branched, substituted or unsubstituted alkenyl, linear or branched, substituted or unsubstituted heteroalkenyl, linear or branched, substituted or unsubstituted alkynyl, substituted or unsubstituted heteroalkynyl, substituted or unsubstituted cycloalkyl, substituted or unsubstituted heterocycloalkyl, substituted or unsubstituted aryl, substituted or unsubstituted heteroaryl, linear or branched, substituted or unsubstituted alkylaryl, linear or branched, substituted or unsubstituted heteroalkylaryl, each of these groups having up to 20 carbon atoms; and $L_1$, $L_2$, $L_3$, $L_4$, and $L_5$ are independently metal-coordinating ligands selected from the group consisting of neutral ligands, anionic ligands and mixed ligands;

comprising contacting a compound having the structure of formula (III)

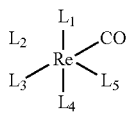

(III)

with a compound having the structure of formula (IV)

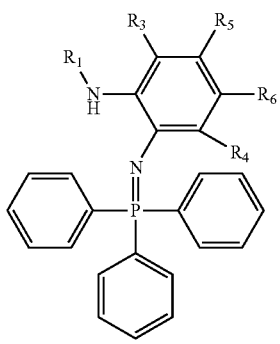

(IV)

to form the complex having the structure of formula (II).

The term "contacting" or "bringing into contact" as used interchangeably herein generally refers to access from one component, reagent, analyte or sample to another. For example, contacting may involve mixing a solution. This solution, which includes a component, reagent, analyte or sample, may also include another component or reagent such as dimethyl sulfoxide (DMSO), a detergent or human serum albumin, which facilitates mixing, interaction, uptake or any other physical or chemical phenomenon that is beneficial. In a non-limiting embodiment, "contacting" takes place in a liquid environment.

Conditions for carrying out the manufacturing process, in particular for the synthesis of compounds (III) and (IV), are known to the skilled person. In non-limiting embodiments, compounds (III) and (IV) are dissolved in toluene or THF in a protective gas atmosphere ($N_2$) in a molar ratio of 1:1 and stirred at room temperature for 24 hours. The solvent is removed in vacuo and the crude product (compound (II)) is purified by column chromatography on silica gel. The compound (II) can be further converted to compound (I). The skilled artisan is familiar with the respective reactions.

A sixth aspect is directed to a method for identifying a molecule, which interacts with the complex, comprising a) providing a complex, wherein $R_5$ is a linker group; and b) immobilizing the complex of a) on a solid support, wherein the solid support binds the complex via the linker group;

c) contacting the immobilized complex with a solution comprising the molecules of interest; and (d) releasing the molecules interacting with the immobilized complex and identifying those molecules.

In various embodiments, the linker group is

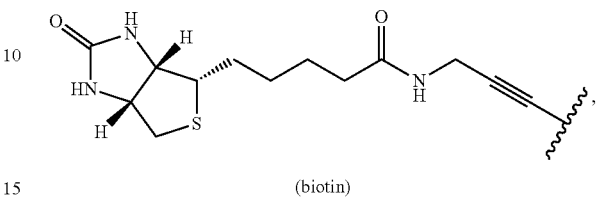

(biotin)

and the solid carrier comprises avidin and/or streptavidin.

The term "immobilization", as used in the present description, refers to the attachment or adherence of one or more biomolecules to the activated surface of a solid support, including attachment or adhesion to the activated inner surface of the support, in case it is porous.

"Solid support", as used herein, refers to any solid surface, to which the compounds may be bonded, such as latex beads, dextran beads, polystyrene surfaces, polypropylene surfaces, polyacrylamide gel, gold surfaces, glass surfaces and silicon discs.

The term "linker group", as used herein, refers to any agent or molecule connecting the inventive compounds and the solid support. In non-limiting embodiments, all molecular bonds, i.e. within the linker group, to the inventive compounds as well as the solid support, are covalent and stable under the conditions of the identification process.

The term "avidin" as used herein refers to any biotin-binding compound, such as avidin, streptavidin, any modified or mutated avidin produced by laboratory techniques, which is capable of binding biotin or a functional equivalent of biotin. Streptavidin is a special subtype of avidin.

The term "streptavidin", as used herein, comprises wild type streptavidin, streptavidin muteins, and streptavidin-like polypeptides, unless otherwise specified. Wild type streptavidin (wt streptavidin) is the amino acid sequence as defined by Argarana et al., Nucleic Acids Res. 14 (1986) 1871-1882. Streptavidin muteins are polypeptides, which differ from the sequence of wild-type streptavidin by one or more amino acid substitutions, deletions or additions and which retain the binding properties of wt streptavidin. Streptavidin-like polypeptides and streptavidin muteins are polypeptides, which are essentially immunologically equivalent to wild-type streptavidin and in particular can bind biotin, biotin derivative or biotin analogues with the same or different affinity as wt streptavidin. Streptavidin-like polypeptides or streptavidin muteins may contain amino acids that are not part of wild-type streptavidin or may contain only part of wild-type streptavidin.

The term streptavidin also includes streptavidin tetramers and streptavidin dimers, in particular streptavidin homotetramers, streptavidin homodimers, streptavidin heterotetramers, and strepavidin heterodimers. Each subunit usually has a binding site for biotin or biotin analogues or for streptavidin-binding peptides.

Examples of streptavidin or streptavidin muteins are disclosed in WO 86/02077, DE 19641876 A1, U.S. Pat. No. 6,022,951, WO 98/40396, and WO 96/24606.

The term "at least 1", as used herein, refers to 1 or more, 2 or more, 3 or more, 4 or more, 5 or more, 6 or more, 7 or more, 8 or more, 9 or more, 10 or more, 100 or more or 1000 or more.

EXAMPLES

Materials and Methods
Materials

All chemicals used were purchased in reagent or analytical quality from commercial suppliers and used without further purification. Solvents were used either as purchased or dried (molecular sieve). All reactions were performed using standard Schlenk techniques in an inert gas atmosphere ($N_2$), unless otherwise specified. $^1H$, $^{13}C\{^1H\}$ and $^{31}P$ NMR spectra were recorded on Bruker spectrometers DPX 200 ($^1H$: 200 MHz, $^{13}C$: 50 MHz), DPX 250 ($^1H$: 250 MHz, $^{13}C$: 63 MHz, $^{31}P$: 101 MHz) or DRX 400 ($^1H$: 400 MHz, $^{13}C$: 100 MHz). Chemical shifts δ are expressed in ppm vs TMS ($^1H$, $^{13}C$) or $H_3PO_4$ ($^{31}P$). Solvent peaks of deuterated solvents were used as a secondary reference. The following abbreviations for multiplicity are used: s (singlet), d (doublet), dd (doublet of doublets), t (triplet), m (multiplet), br (wide). IR spectra were recorded on a Bruker Tensor 27 FT-IR spectrometer equipped with an ATR (attenuated total reflection) unit. Mass spectra were recorded on a Bruker Esquire 6000 spectrometer using an electrospray ionization source (ESI). X-ray diffraction experiments on suitable crystals were performed using a Rigaku Mercury 375 R/MCCD (XtaLAB mini) or Oxford Xcalibur2 (MoKα, =0.71073 Å). The structures were solved by direct methods (ShelXS) and refined against $F^2$ (all reflexes, ShelXL97 and ShelXL2014). Hydrogen atoms were added at calculated positions. For the structural solutions of compounds 4c and 6a the program package PLATON was used for the treatment of strongly disordered solvent molecules (SQEEZE).

Photophysical Measurements

All solvents used for photophysical measurements were of spectroscopic quality and were used as obtained. At least 3 consecutive Freeze-pump-Thaw passes were performed to degas solvents. Absorption spectra were recorded on either a Jasco V-770 UV-VIS-NIR photometer or a Varian Cary 100 UV-VIS spectrophotometer. Steady state emission spectra were recorded on a Jasco FP-8300 spectrofluorimeter. The emission spectra were corrected for the spectral sensitivity of the detection system. Luminescence lifetime was determined using a FluoTime 200 TCSPC system consisting of an LDH-P-C-405 laser diode with a PDL 800-B laser driver and an air-cooled PMT detector (PMA series, PicoQuant). The obtained data were analyzed with the FluoFit software package (PicoQuant). To determine the quantum yield, the approach of Demas and Crosby[45] was used and $Ru(bipy)_3Cl_2$ in water (φ=0.044)[46] and quinine sulfate in $H_2SO_4$ (Φ=0.54)[47] served as reference compounds. Quantum yields of the investigated compounds were calculated in comparison to the reference compounds according to the following equation:

$$\theta_X = \theta_{Ref} \frac{G_X}{G_{Ref}} \left(\frac{\eta_X}{\eta_{Ref}}\right)^2$$

The indices "X" and "Ref" indicate the compound to be examined and the references. Θ is the quantum yield, η stands for the refractive index of the solvent. G is determined by plotting the absorption of a series of dilutions (absorption <0.1) against the integrated emission intensity. G is obtained as the gradient of a linear approximation of the plotted data.

Determination of the Minimum Inhibitory Concentration (MHK)

Minimum inhibitory concentrations (MHK) were determined against the Gram-positive strains *Bacillus subtilis* DSM 402, *Staphylococcus aureus* DSM 20231, and *Staphylococcus aureus* ATCC 43300 (MRSA). As Gram-negative strains, *Escherichia coli* DSM 30083, *Acinetobacter baumannii* DSM 30007, and *Pseudomonas aeruginosa* DSM 50071 were used. *E. coli*, *A. baumannii*, *S. aureus* and *B. subtilis* were cultured in Mueller-Hinton liquid medium, while *P. aeruginosa* was cultured in Mueller-Hinton II liquid medium. The compounds were stored in DMSO and in solutions of 10 mg/ml. Serial dilution was performed with a Tecan Freedom Evo 75 Liquid Handling Workstation (final concentrations 0.5 to 512 µg/ml). Serial dilutions were inoculated with $5 \times 10^5$ bacteria/ml from late exponential cultures (total volume 200 µl per well). Cells were incubated at 37° C. for 16-18 h. The lowest concentration that prevents visible bacterial growth is indicated as MHK.

Synthesis

2-Azidoaniline was synthesized from aniline via a mild copper-catalyzed azidation reaction according to Jiao and collaborators. The analytical data obtained correspond to literature values.[48]

Reductive Amination with 2-Azidoaniline and Aromatic Aldehydes

General procedure: According to a modified procedure of Shah et al.[49], 2-azidoaniline (1 equiv.) and a corresponding aromatic aldehyde (1 equiv.) were dissolved in 1,2-dichloroethane in a nitrogen atmosphere. Sodium triacetoxyborohydride (1.4 equiv.) was then added in small portions and the resulting solution was stirred for 24 hours at room temperature. The reactions were quenched by adding a concentrated aqueous $NaHCO_3$ solution and the resulting suspension was extracted with dichloromethane. The organic phase was dried over sodium sulfate and concentrated in vacuo. The crude product was purified by column chromatography on silica gel using a mixture of petroleum ether (PE) and ethyl acetate (EtOAc).

1b: The general procedure was applied with 2-azidoaniline (200 mg, 1.49 mmol), benzaldehyde (158 mg, 1.49 mmol) and 442 mg sodium triacetoxyborohydride (2.1 mmol). After purification by column chromatography on silica gel (PE: EtOAc 25:1), a brown oil (190 mg, 57%) was obtained as product. $C_{13}H_{12}N_4$ (224.27 g/mol). $R_f$ ($SiO_2$, PE:EtOAc 25:1, detection: UV)=0.5. $^1H$ NMR (200 MHz, $CDCl_3$) δ [ppm]=7.28-7.18 (m 5H), 6.99-6.88 (m, 2H), 6.72-6.66 (m, 1H), 6.58-6.54 (m, 1H) 4.48 (br s, 1H, NH), 4.35 (s, 2H, $CH_2$). $^{13}C$ NMR (50.3 MHz, $CDCl_3$) δ [ppm]=139.8, 139.1, 128.8, 127.5, 127.4, 126.0, 124.8, 118.0, 117.5, 111.3, 48.0.

1c: The general procedure with 2-azidoaniline (350 mg, 2.6 mmol), 2,4,6-trimethylbenzaldehyde (385 mg, 2.6 mmol) and sodium triacetoxyborohydride (785 mg, 3.6 mmol) was used. After column chromatography ($SiO_2$, PE:EtOAc 20:1), the product was obtained in the form of a beige solid (410 mg, 58%). $C_{16}H_{18}N_4$ (266.35 g/mol). $R_f$ ($SiO_2$, PE:EtOAc 20:1, detection: UV)=0.6. $^1H$ NMR (250 MHz, $CDCl_3$) δ [ppm]=7.15-7.08 (m, 1H), 7.06-7.02 (m, 1H), 6.91 (s, 2H), 6.81 (s, 1H), 6.78 (s, 1H), 4.19 (s, 2H, $CH_2$), 2.34 (s, 6H, 2×$CH_3$), 2.30 (s, 3H, $CH_3$). $^{13}C$ NMR (62.5 MHz, $CDCl_3$) δ [ppm]=140.0, 137.7, 137.5, 131.7, 129.3, 126.1, 124.9, 118.0, 117.5, 42.5, 21.1, 19.6. IR (ATR) v=3376 (m), 2868 (m), 2126 (s), 1579 (s), 1424 (s), 888 (s), 858 (m).

Preparation of Phosphinimines 2a-2c

General procedure: Azidoaniline or its derivatives were dissolved in toluene. Within 10 minutes a solution of triphenylphosphine (1.02 equiv.) in toluene was added using a syringe. The solution was stirred at room temperature for 24 hours. The solvent was removed in vacuo and the crude product is purified by column chromatography on silica gel.

2a: The general procedure was performed with 2-azidoaniline (224 mg, 1.67 mmol) and $PPh_3$ (440 mg, 1.7 mmol). After column chromatography ($SiO_2$, gradient hexane:EtOAc 4:1 to 0:1), the product was obtained in the form of an orange crystalline solid (550 mg, 89%). $C_{24}H_{21}N_2P$ (368.42 g/mol), $^1$H NMR (250 MHz, $CDCl_3$) δ [ppm]=7.82-7.72 (m, 6H), 7.56-7.42 (m, 9H), 6.75-6.70 (m, 1H), 6.60-6.52 (m, 1H), 6.41-6.31 (m, 2H), 4.36 (br s, 2H, $NH_2$). $^{13}$C NMR (63 MHz, $CDCl_3$) δ [ppm]=141.9 (d, $^3J_{CP}$=20.4 Hz, C—$NH_2$), 137.8 ($C_{Anilin}$), 132.7 (d, $^2J_{CP}$=9.7 Hz, 6×$C^{meta}$), 131.8 (d, $^4J_{CP}$=2.9 Hz, 3×$C^{para}$), 131.3 (d, $^1J_{CP}$=99.7 Hz, 3×C—P), 128.7 (d, $^3J_{CP}$=12 Hz, 6×$C^{meta}$), 120.4 (d, J=9.1 Hz), 118.5 ($C_{Aniline}$), 118.2 ($C_{Aniline}$), 114.2 ($C_{Aniline}$). $^{31}$P NMR (101 MHz, $CDCl_3$) δ [ppm]=4.8. MS (ESI+): m/z=368.96 [M+H]t IR (ATR) v=3453 (m), 3351 (m), 3053 (m), 1595 (s), 1493 (s), 1435 (s), 1250 (s), 1104 (s), 690 (s).

2b: The general procedure was performed with 2-azido-N-benzylaniline (200 mg, 0.90 mmol) and $PPh_3$ (239 mg, 0.91 mmol). After column chromatography (PE:EtOAc 4:1), the product was obtained in the form of an orange solid (310 mg, 76%). $C_{31}H_{27}N_2P$ (458.54 g/mol). $R_f$ ($SiO_2$, PE:EtOAc 4:1, detection: UV)=0.3. $^1$H NMR (250 MHz, $CDCl_3$) δ [ppm]=7.91-7.80 (m, 6H), 7.65-7.48 (m, 11H), 7.45-7.28 (m, 3H), 6.67-6.57 (m, 2H), 6.50-6.44 (m, 1H) 6.37-6.29 (m, 1H), 5.50 (br s, 1H, NH), 4.54 (s, 2H, $CH_2$). $^{13}$C NMR (63 MHz, $CDCl_3$) δ [ppm]=144.1 (d, $^3J_{CP}$=19.8 Hz, C—NH), 141.7 ($C_{Phenyl}$), 137.8 ($C_{Aniline}$), 133.0 (d, $^2J_{CP}$=9.7 Hz, 6×$C^{ortho}$), 132.3 (d, $^4J_{CP}$=2.9 Hz, 3×$C^{para}$), 131.7 (d, $^1J_{CP}$=99.6 Hz, 3×C—P), 129.2 (d, $^3J_{CP}$=11.9 Hz, 6×$C^{meta}$), 128.9 ($C^{phenyl}$), 127.7 ($C^{phenyl}$), 127.2 ($C^{phenyl}$), 119.4 (d, J=9.3 Hz), 118.9 ($C_{Aniline}$), 116.7 ($C_{Aniline}$), 109.6 ($C_{Aniline}$), 48.9 ($CH_2$). $^{31}$P NMR (101 MHz, $CDCl_3$) δ [ppm]=4.6. MS (ESI+): m/z=458.9 [M+H]$^+$. IR (ATR) v=3022 (m), 1736 (m), 1569 (s), 1495 (s), 1417 (s), 1364 (m), 1302 (m), 1229 (m), 736 (m).

2c: The general procedure was performed with 2-azido-N-(2,4,6-trimethylbenzyl)aniline (272 mg, 1 mmol) and $PPh_3$ (265 mg, 1.02 mmol). After column chromatography (gradient hexane:EtOAc 4:1), the product was obtained in the form of a yellow solid (370 mg, 72%). $C_{34}H_{33}N_2P$ (500, 24 g/mol). $^1$H NMR (250 MHz, $CD_2Cl_2$) δ [ppm]=7.70-7.60 (m, 6H), 7.56-7.49 (m, 4H), 7.44-7.36 (m, 5H), 6.89 (s, 2H), 6.69-6.59 (m, 2H), 6.33-6.21 (m, 2H), 4.24 (s, 2H), 2.36 (s, 6H, 2×$CH_3$), 2.30 (s, 3H, $CH_3$). $^{13}$C NMR (50 MHz, $CD_2Cl_2$) δ [ppm]=145.0 (J=19.0 Hz), 137.6, 137.5, 136.8, 134.2, 132.8 ($^2J_{CP}$=9.5 Hz, 6×$C^{ortho}$), 132.1 (d, $^4J_{CP}$=2.8 Hz, 3×$C^{para}$), 131.5 (d, $^1J_{cp}$=99.0 Hz, 3×C—P), 129.3, 128.9 (d, $^3J_{cp}$=12.0 Hz, 6×$C^{meta}$), 119.1 (d, J=8.5 Hz), 118.9, 116.5, 109.6, 43.7 ($CH_2$), 21.3 ($CH_3$), 19.8 (2×$CH_3$). $^{31}$P NMR (101 MHz, $CDCl_3$) δ [ppm]=3.1. MS (ESI+): m/z=501.0 [M+H]$^+$, 522.9 [M+Na]$^+$. IR (ATR) v=1583 (m), 1510 (m), 1423 (m), 1312 (m), 1264 (s), 1108 (s), 1021 (s), 862 (m), 717 (s), 694 (s).

Preparation of $Re(CO)_4$(NHC)Br Complexes

General procedure: Phosphinimine (1 equiv.) and $Re(CO)_5Br$ (1 equiv.) are dissolved in toluene or THF under $N_2$ and stirred for 24 hours at room temperature. The solvent is removed in vacuo and the crude product is purified by column chromatography on silica gel.

3a: The general procedure was employed with phosphinimine 2a (200 mg, 0.54 mmol) and $Re(CO)_5Br$ (220 mg, 0.54 mmol). The product was obtained in the form of a beige solid (230 mg, 86%). $C_{11}H_6N_2O_4ReBr$ (496.29 g/mol). $R_f$ ($SiO_2$, Hexan:EtOAc 9:1, Detection: UV)=0.2. $^1$H NMR (200 MHz, $CDCl_3$) δ [ppm]=10.41 (s, 2H, NH), 7.57-7.50 (m, 2H, $H_{Bim}$), 7.42-7.35 (m, 2H, $H_{Bim}$). $^{13}$C NMR (50 MHz, $CD_2Cl_2$) δ [ppm]=187.5 (CO), 185.7 (CO), 185.4 (CO), 171.9 ($C_{carbene}$), 133.8 ($C_{Bim}$), 124.9 ($C_{Bim}$), 112.1 ($C_{Bim}$). IR (ATR) v=3354 (m), 3292 (m), 2103 (m), 1977 (s), 1907 (s), 1887 (s), 1451 (s), 724 (s).

3b: The general procedure was applied with phosphinimine 2b (126 mg, 0.28 mmol) and $Re(CO)_5Br$ (112 mg, 0.28 mmol). The product was obtained in the form of a beige solid (137 mg, 85%). $C_{18}H_{12}N_2O_4ReBr$. (586.42 g/mol). $R_f$ ($SiO_2$, Hexan:EtOAc 4:1, Detection: UV)=0.4. $^1$H NMR (200 MHz, $CDCl_3$) δ [ppm]=11.35 (s, 1H, NH), 7.54-7.50 (m, 1H, $H_{Ph}$), 7.36-7.21 (m, 6H, $H_{Ph}$+$H_{Bim}$), 7.04-7.00 (m, 2H, $H_{Bim}$), 5.67 (s, 2H, $CH_2$). $^{13}$C (50 MHz, $CDCl_3$) δ [ppm]=186.1 (CO), 185.7 (CO), 184.6 (CO), 175.9 ($C_{carbene}$), 135.0 ($C_{Bim}$), 134.9 ($C_{Bim}$), 133.5 ($C_{Ph}$), 129.3 ($C_{Ph}$), 128.4 ($C_{Ph}$), 126.1 ($C_{Ph}$), 124.7 ($C_{Bim}$), 124.3 ($C_{Bim}$), 112.1 ($C_{Bim}$), 111.5 ($C_{Bim}$), 51.8 ($CH_2$). IR (ATR) v=3275 (w), 2105 (s), 1972 (s), 1915 (s), 1748 (m), 1728 (m), 1433 (m), 1370 (m), 1228 (m), 723 (m), 670 (m).

3c: The general procedure was applied with phosphinimine 2c (370 mg, 0.74 mmol) and $Re(CO)_5Br$ (300 mg, 0.74 mmol) in THF. The product was obtained in the form of a beige solid (270 mg, 58%). $C_{21}H_{18}N_2O_4ReBr$ (628.5 g/mol). $R_f$ ($SiO_2$, Hexan:EtOAc 9:1, Detection: UV)=0.3. $^1$H NMR (200 MHz, $CDCl_3$) δ [ppm]=11.27 (s, 1H, NH), 7.48-7.44 (m, 1H, $H_{Bim}$), 7.23-7.18 (m, 1H, $H_{Bim}$), 7.02-6.97 (m, 1H, $H_{Bim}$), 6.94 (s, 2H, $H_{Ph}$), 6.47-6.40 (m, 1H, $H_{Bim}$), 5.70 (s, 2H, $CH_2$), 2.34 (s, 3H, $CH_3$), 2.23 (s, 6H, 2×$CH_3$). $^{13}$C NMR (50 MHz, $CDCl_3$) δ [ppm]=186.2 (CO), 186.1 (CO), 185.1 (CO), 175.8 ($C_{carbene}$), 139.1 ($C_{Ph}$), 137.9 ($C_{Ph}$), 134.4 ($C_{Bim}$), 133.7 ($C_{Bim}$), 130.2 ($C_{Ph}$), 127.3 ($C_{Ph}$), 124.2 ($C_{Bim}$), 123.9 ($C_{Bim}$), 112.2 ($C_{Bim}$), 111.8 ($C_{Bim}$), 51.1 ($CH_2$), 21.2 ($CH_3$), 20.4 (2×$CH_3$). IR (ATR) v=3280 (w), 2923 (w), 1982 (s), 1918 (s), 1494 (m), 1429 (m), 1338 (m), 1260 (m), 1193 (m), 720 (m).

Preparation of $[Re(CO)_3(NHC)L]^+$ Complexes

General procedure: Rhenium complexes 3a-3c (1 equiv.) and the corresponding bisimine ligand (1.05 equiv.) are dissolved/suspended in toluene and stirred at 100° C. for 4 hours. After cooling to ambient temperature, the yellowish precipitate is isolated by filtration, washed intensively with cold ether, and dried in vacuo to obtain the product with high purity. In cases where the products do not precipitate immediately, cold ether may be added to facilitate precipitation.

4a: The general procedure was performed with complex 3a (100 mg, 0.2 mmol) and 2'2-bipyridine (32.8 mg, 0.21 mmol). The product was obtained in the form of a yellow solid (100 mg, 80%). $C_{20}H_{14}N_4O_3ReBr$ (624.46 g/mol). $^1$H NMR (400 MHz, $DMSO[d_6]$) δ [ppm]=12.73 (s, 2H, NH), 9.25 (d, J=5 Hz, 2H, $H_{Bipy}$), 8.71 (d, J=8.1 Hz, 2H, $H_{Bipy}$), 8.33 (td, J=7.8 Hz, 1 Hz, 2H, $H_{Bipy}$), 7.84 (m, 2H, $H_{Bipy}$), 7.41 (dd, J=6.0 Hz, 3.0 Hz, 2H, $H_{Bim}$), 7.22 (dd, J=6.0 Hz, 3.0 Hz, 2H, $H_{Bim}$). $^{13}$C NMR (100 MHz, $DMSO[d_6]$) δ [ppm]=196.1 (CO), 192.8 (CO), 180.7 ($C_{carbene}$), 155.0 ($C_{Bipy}$), 154.1 ($C_{Bipy}$), 140.2 ($C_{Bim}$), 133.0 ($C_{Bipy}$), 128.2 ($C_{Bim}$), 124.5 ($C_{Bipy}$), 123.5 ($C_{Bipy}$), 111.7 ($C_{Bim}$). MS (ESI+): m/z=544.8 [M-Br]$^+$. IR (ATR) v=3646 (w), 3061 (m), 2019 (s), 1914 (s), 1890 (s), 1446 (s), 759 (s).

5a: The general procedure was performed with complex 3a (26 mg, 0.05 mmol) and phenanthroline (11 mg, 0.059 mmol). The product was obtained in the form of a yellow solid (25 mg, 75%). $C_{22}H_{14}N_4O_3ReBr$ (648.49 g/mol). $^1H$ NMR (400 MHz, DMSO[$d_6$]) δ [ppm]=12.71 (s, 2H, NH), 9.68 (d, J=4.8 Hz, 2H, $H_{Phen}$), 8.97 (d, J=8.2 Hz, 2H, $H_{Phen}$), 8.28 (2, 2H, $H_{Phen}$), 8.20 (dd, J=8.2, 5.2 Hz, 2H, $H_{Phen}$), 7.32 (dd, J=6.0, 3.2 Hz, 2H, $H_{Bim}$), 7.15 (dd, J=6.0, 3.2 Hz, 2H, $H_{Bim}$). $^{13}C$ NMR (100 MHz, DMSO[$d_6$]) δ [ppm]=196.1 (CO), 192.8 (CO), 180.7 ($C_{carbene}$), 155.0 ($C_{Phen}$), 154.6 ($C_{Phen}$), 139.3 ($C_{Phen}$), 132.9 ($C_{Bim}$), 130.4 ($C_{Phen}$), 127.8 ($C_{Phen}$), 126.8 ($C_{Phen}$), 123.4 ($C_{Bim}$), 111.6 ($C_{Bim}$). MS (ESI+): m/z=568.8 [M-Br]$^+$. IR (ATR) v=3105 (w), 2025 (s), 1920 (s), 1887 (s), 1374 (m), 842 (m), 748 (m).

6a: The general procedure was performed with complex 3a (50 mg, 0.1 mmol) and 4,4'-di-tert-butyl-2,2'-bipyridine (28 mg, 0.105 mmol). The product was obtained in the form of a yellow solid (62 mg, 83%). $C_{28}H_{30}N_4O_3ReBr$ (736.67 g/mol). $^1H$ NMR (400 MHz, DMSO[$d_6$]) δ [ppm]=12.70 (s, 2H, NH), 9.11 (d, J=5.8 Hz, 2H, $H_{Bipy}$), 8.69 (s, 2H, $H_{Bipy}$), 7.81 (d, J=4.6 Hz, 2H, $H_{Bipy}$), 7.43 (m, 2H, $H_{Bim}$), 7.22 (m, 2H, $H_{Bim}$), 1.42 (s, 18H, $H_{tBu}$). $^{13}C$ NMR (100 MHz, DMSO[$d_6$]) δ [ppm]=196.2 (CO), 192.8 (CO), 180.9 ($C_{carben}$), 164.2 ($C_{Bipy}$), 155.1 ($C_{Bipy}$), 153.6 ($C_{Bipy}$), 133.0 ($C_{Bim}$), 124.9 ($C_{Bim}$), 123.4 ($C_{Bipy}$), 121.7 ($C_{Bipy}$), 111.7 ($C_{Bim}$), 35.7 ($C_{tBu}$), 29.9 (6×$CH_3$). MS (ESI+): m/z=656.9 [M-Br]$^+$. IR (ATR) v=2967 (m), 2016 (s), 1898 (s), 1617 (m), 1443 (m), 1371 (m), 848 (m), 746 (m).

7a: The general procedure was performed with complex 3a (40 mg, 0.08 mmol) and bathophenanthroline (28 mg, 0.084 mmol). The product was obtained in the form of a yellow solid (42 mg, 65%). $C_{34}H_{22}N_4O_3ReBr$ (800.68 g/mol). $^1H$ NMR (400 MHz, DMSO[$d_6$]) δ [ppm]=12.88 (s, 2H, NH), 9.75 (d, J=5.4 Hz, 2H, $H_{Phen}$), 8.18 (d, J=5.4 Hz, 2H, $H_{Phen}$), 8.12 (s, 2H, $H_{Phen}$), 7.72-7.64 (m, 10H, $H_{Phen}$), 7.42-7.40 (m, 2H, $H_{Bim}$), 7.21-7.19 (m, 2H, $H_{Bim}$). $^{13}C$ NMR (100 MHz, DMSO[$d_6$]) δ [ppm]=196.1 (CO), 192.6 (CO), 180.5 ($C_{carben}$), 154.6 ($C_{Phen}$), 150.3 ($C_{Phen}$), 146.6 ($C_{Phen}$), 135.2 ($C_{Phen}$), 133.0 ($C_{Bim}$), 129.8 ($C_{Phen}$), 129.1 ($C_{Phen}$), 128.1 ($C_{Phen}$), 126.8 ($C_{Phen}$), 125.7 ($C_{Phen}$), 123.4 ($C_{Bim}$), 111.7 ($C_{Bim}$). MS (ESI+): m/z=720.8 [M-Br]$^+$. IR (ATR) v=2976 (w), 2017 (s), 1897 (s), 1623 (m), 1598 (m), 1446 (m), 1418 (m), 849 (m), 749 (m), 701 (m).

4b: The general procedure was performed with complex 3b (40 mg, 0.08 mmol) and 2'2-bipyridine (28 mg, 0.084 mmol). The product was obtained in the form of a yellow solid (42 mg, 65%). $C_{27}H_{20}N_4O_3ReBr$ (714.59 g/mol). $^1H$ NMR (400 MHz, DMSO[$d_6$]) δ [ppm]=12.74 (s, 1H, NH), 9.32 (d, J=4.9 Hz, 2H, $H_{Bipy}$), 8.59 (d, J=8.2 Hz, 2H, $H_{Bipy}$), 8.15-8.13 (m, 2H, $H_{Bipy}$), 7.63-7.59 (m, 2H, $H_{Bipy}$), 7.48 (d, J=8.1 Hz, 1H, $H_{Bim}$), 7.24 (t, J=7.7 Hz, 1H, $H_{Ph}$), 7.15-7.02 (m, 5H, $H_{Bim}$ $H_{Ph}$), 6.43 (d, J=7.4 Hz, 2H, $H_{Ph}$), 5.69 (s, 2H, $CH_2$). $^{13}C$ NMR (100 MHz, DMSO[$d_6$]) δ [ppm]=195.2 (CO), 191.9 (CO), 183.4 ($C_{carben}$), 155.1 ($C_{Bipy}$), 154.1 ($C_{Bipy}$), 140.1 ($C_{Bipy}$), 135.4 ($C_{Ph}$), 133.8 ($C_{Bim}$), 133.0 ($C_{Bim}$), 128.4 ($C_{Ph}$), 128.2 ($C_{Bipy}$), 127.2 ($C_{Ph}$), 124.9 ($C_{Ph}$), 124.4 ($C_{Bipy}$), 124.1 ($C_{Bim}$), 123.6 ($C_{Bim}$), 112.2 ($C_{Bim}$), 111.8 ($C_{Bim}$), 50.5 ($CH_2$). MS (ESI+): m/z=634.7 [M-Br]$^+$, 606.8 [M-Br—CO]$^+$. IR (ATR) v=3061 (w), 2024 (s), 1948 (s), 1923 (s), 1601 (m), 1469 (m), 1429 (m), 1375 (m), 1344 (m), 762 (m), 741 (m), 728 (s), 613 (m).

5b: The general procedure was performed with complex 3b (30 mg, 0.05 mmol) and phenanthroline (10 mg, 0.055 mmol). The product was obtained in the form of a yellow solid (29 mg, 64%). $C_{29}H_{20}N_4O_3ReBr$ (738.62 g/mol). $^1H$ NMR (250 MHz, DMSO[$d_6$]) δ [ppm]=12.89 (s, 1H, NH), 9.76 (d, J=4.4 Hz, 2H, $H_{Phen}$), 8.76 (d, J=8.0 Hz, 2H, $H_{Phen}$), 8.21 (s, 2H, $H_{Phen}$), 7.93-7.88 (m, 2H, $H_{Phen}$), 7.44 (d, J=8.1 Hz, 1H, $H_{Bim}$), 7.22-6.81 (m, 6H, $H_{Phen}$+$H_{Bim}$), 6.06 (d, J=7.2 Hz, 2H, $H_{Phen}$), 5.73 (s, 2H, $CH_2$). $^{13}C$ NMR (63 MHz, DMSO[$d_6$]) δ [ppm]=195.2 (CO), 192.0 (CO), 183.3 ($C_{carbene}$), 155.1 ($C_{Phen}$), 145.6 ($C_{Phen}$), 139.2 ($C_{Phen}$), 135.4 ($C_{Bim}$), 133.8 ($C_{Bim}$), 132.9 ($C_{Ph}$), 130.5 ($C_{Phen}$), 128.2 ($C_{Ph}$), 127.8 ($C_{Phen}$), 127.1 ($C_{Ph}$), 126.6 ($C_{Phen}$), 124.4 ($C_{Ph}$), 124.1 ($C_{Bim}$), 123.5 ($C_{Bim}$), 112.1 ($C_{Bim}$), 111.7 ($C_{Bim}$), 50.3 ($CH_2$). MS (ESI+): m/z=658.7 [M-Br]$^+$, 630.8 [M-Br—CO]$^+$. IR (ATR) v=2970 (w), 2024 (s), 1932 (s), 1903 (s), 1740 (m), 1434 (m), 1368 (m), 1241 (m).

7b: The general procedure was performed with complex 3b (30 mg, 0.05 mmol) and bathophenanthroline (20 mg, 0.06 mmol). The product was obtained in the form of a yellow solid (39 mg, 96%). $C_{41}H_{28}N_4O_3ReBr$ (890.81 g/mol). $^1H$ NMR (400 MHz, DMSO[$d_6$]) δ [ppm]=13.14 (s, 1H, NH), 9.83 (d, J=5.4 Hz, 2H, $H_{Phen}$), 8.06 (s, 2H, $H_{Phen}$), 7.87 (d, J=5.4 Hz, 2H, $H_{Phen}$), 7.67-7.60 (m, 10H, $H_{Phen}$), 7.53 (d, J=8.1 Hz, 1H, $H_{Bim}$), 7.25-7.21 (m, 1H, $H_{Bim}$), 7.12-7.08 (m, 1H, $H_{Ph}$), 7.00-6.98 (m, 1H, $H_{Bim}$), 6.92-6.90 (m, 1H, $H_{Bim}$), 6.83-6.79 (m, 2H, $H_{Ph}$), 6.12 (d, J=7.2 Hz, 2H, $H_{Ph}$h), 5.85 (s, 2H, $CH_2$). $^{13}C$ NMR (63 MHz, DMSO[$d_6$]) δ [ppm]=195.2 (CO), 191.7 (CO), 183.0 ($C_{carbene}$), 154.7 ($C_{Phen}$), 150.3 ($C_{Phen}$), 146.6 ($C_{Phen}$), 135.2 ($C_{Bim}$), 135.0 ($C_{Ph}$), 134.0, 133.0 ($C_{Bim}$), 130.0 ($C_{Phen}$), 129.8 ($C_{Ph}$), 129.0 ($C_{Phen}$), 128.0, 127.2, 126.6 ($C_{Ph}$), 125.6, 124.4, 124.1 ($C_{Bim}$), 123.5 ($C_{Bim}$), 112.2 ($C_{Bim}$), 111.7 ($C_{Bim}$), 50.3 ($CH_2$). MS (ESI+): m/z=810.7 [M-Br]$^+$, 782.8 [M-Br—CO]$^+$. IR (ATR) v=2368 (m), 2019 (s), 1897 (s), 1621 (s), 1517 (m), 1492 (m), 1425 (m), 907 (m), 765 (m), 620 (m).

4c: The general procedure was performed with complex 3c (50 mg, 0.08 mmol) and 2'-bipyridine (13 mg, 0.085 mmol). The product was obtained in the form of a yellow solid (43 mg, 79%). $C_{30}H_{26}N_4O_3ReBr$ (756.67 g/mol). $^1H$ NMR (400 MHz, DMSO[$d_6$]) δ [ppm]=12.68 (s, 1H, NH), 9.92 (d, J=5.1 Hz, 2H, $H_{Bipy}$), 8.97 (d, J=8.2 Hz, 2H, $H_{Bipy}$), 8.28 (s, 2H, $H_{Bipy}$), 8.17 (dd, J=8.3, 5.2 Hz, 2H, $H_{Bipy}$), 7.34 (d, J=8.1 Hz, 1H, $H_{Bim}$), 7.07 (t, J=7.6 Hz, 1H, $H_{Bim}$), 6.87-6.82 (m, 3H, $H_{Bim}$+$H_{Ph}$), 6.12 (d, J=8.4 Hz, 1H, $H_{Bim}$), 5.38 (s, 2H, $CH_2$), 2.22 (s, 3H, $CH_3$), 1.76 (s, 6H, 2×$CH_3$). $^{13}C$ NMR (100 MHz, DMSO[$d_6$]) δ [ppm]=195.7 (CO), 186.6 (CO), 184.0 ($C_{carbene}$), 155.6 ($C_{Bipy}$), 145.9 ($C_{Bipy}$), 139.7 ($C_{Ph}$), 137.5, 136.8 ($C_{Ph}$), 133.8 ($C_{Bim}$), 132.9 ($C_{Bim}$), 130.5 ($C_{Ph}$), 129.5 ($C_{Ph}$), 127.9 ($C_{Bipy}$), 127.5 ($C_{Bipy}$), 126.7 ($C_{Bipy}$), 123.6 ($C_{Bim}$), 123.1 ($C_{Bim}$), 112.0 ($C_{Bim}$), 111.4 ($C_{Bim}$), 49.3 ($CH_2$), 20.5 ($CH_3$), 19.0 (2×$CH_3$). MS (ESI+): m/z=676.8 [M-Br]$^+$. IR (ATR) v=3016 (w), 2019 (s), 1924 (s), 1901 (s), 1601 (w), 1438 (m), 753 (m), 731 (m), 694 (m), 619 (w).

5c: The general procedure was performed with complex 3c (30 mg, 0.05 mmol) and phenanthroline (10 mg, 0.055 mmol). The product was obtained in the form of a yellow solid (40 mg, 64%). $C_{32}H_{27}N_4O_3ReBr$ (781.70 g/mol). $^1H$ NMR (250 MHz, DMSO[$d_6$]) δ [ppm]=12.70 (s, 1H, NH), 9.93 (d, J=5.0 Hz, 2H, $H_{Phen}$), 8.98 (d, J=8.2 Hz, 2H, $H_{Phen}$), 8.30 (s, 2H, $H_{Phen}$), 8.19 (dd, J=8.2, 5.1 Hz, 2H, $H_{Phen}$), 7.35 (d, J=8.1 Hz, 1H, $H_{Bim}$), 7.08 (t, J=7.7 Hz, 1H, $H_{Bim}$), 6.88-6.83 (m, 3H, $H_{Bim}$+$H_{Ph}$), 6.14 (d, J=8.4 Hz, 1H, $H_{Bim}$), 5.39 (s, 2H, $CH_2$), 2.23 (s, 3H, $CH_3$), 1.78 (s, 6H, 2×$CH_3$). $^{13}C$ NMR (63 MHz, DMSO[$d_6$]) δ [ppm]=195.7 (CO), 186.6 (CO), 184.0 ($C_{carbene}$), 155.6 ($C_{Phen}$), 145.9 ($C_{Phen}$), 139.7 ($C_{Phen}$), 137.5 ($C_{Ph}$), 136.8 ($C_{Ph}$), 133.8 ($C_{Bim}$), 132.9 ($C_{Bim}$), 130.5 ($C_{Ph}$), 129.5 ($C_{Phen}$), 127.9 ($C_{Phen}$), 127.5 ($C_{Ph}$), 126.7 ($C_{Phen}$), 123.6 ($C_{Bim}$), 123.0 ($C_{Bim}$), 112.0 ($C_{Bim}$), 111.4 ($C_{Bim}$), 49.3 ($CH_2$), 20.5 ($CH_3$), 19.0 (2×$CH_3$). MS (ESI+): m/z=700.7 [M-Br]$^+$, 672.8 [M-Br—CO]$^+$. IR (ATR) v=2964 (w), 2019 (s), 1932 (s), 1924 (s), 1422 (m), 1333 (m), 1185 (m), 851 (m), 768 (m), 722 (m), 620 (m).

7c: The general procedure was performed with complex 3c (50 mg, 0.08 mmol) and bathophenanthroline (28 mg, 0.085 mmol). The product was obtained in the form of a yellow solid (62 mg, 91%). $C_{44}H_{35}N_4O_3ReBr$ (933.90 g/mol). $^1$H NMR (250 MHz, DMSO[$d_6$]) δ [ppm]=12.89 (s, 1H, NH), 9.96 (d, 5.5 Hz, 2H, $H_{Phen}$), 8.12-8.11 (m, 4H, $H_{Phen}$), 7.67 (m, 10H, $H_{Phen}$), 7.41 (d, J=8.0 Hz, 1H, $H_{Bim}$), 7.12 (t, J=7.7 Hz, 1H, $H_{Bim}$), 6.89 (t, J=7.9 Hz, 1H, $H_{Bim}$), 6.81 (s, 2H, $H_{Ph}$), 6.20 (d, J=8.4 Hz, 1H, $H_{Bim}$), 5.47 (s, 2H, $CH_2$), 2.17 (s, 3H, $CH_3$), 1.77 (s, 6H, 2×$CH_3$). $^{13}$C NMR (63 MHz, DMSO[$d_6$]) δ [ppm]=195.8 (CO), 188.6 (CO), 183.8 ($C_{carbene}$), 155.2 ($C_{Phen}$), 150.7 ($C_{Phen}$), 146.9 ($C_{Phen}$), 137.4, 136.7, 135.1, 133.9 ($C_{Bim}$), ($C_{Phen}$), 133.1 ($C_{Bim}$), 129.9, 129.8 ($C_{Phen}$), 129.6, 129.2 ($C_{Phen}$), 128.2, 127.4, 126.6, 125.8 ($C_{Bim}$), 123.6 ($C_{Bim}$), 112.1 ($C_{Bim}$), 111.4 ($C_{Bim}$), 58.2 ($CH_2$), 20.4 ($CH_3$), 18.9 (2×$CH_3$). MS (ESI+): m/z=852.7 [M-Br]$^+$, 825.0 [M-Br—CO]$^+$. IR (ATR) v= 2016 (s), 1924 (s), 1905 (s), 1446 (m), 1332 (m), 845 (m), 763 (m), 739 (m), 698 (m).

Identification of Interaction Partners by Immobilization of Biotin-DS50

*B. subtilis* 168 was grown to exponential phase ($OD_{500}$=0.5) in 500 ml Belitzky Minimal Medium (BMM) with 0.78 mM tryptophan at 37° C. while shaking continuously. Cells were harvested by centrifugation, resuspended in 3 ml lysis buffer (100 mM Tris/HCl, pH 8.1 mM dithiotreitol (DTT), 1 mM β-mercaptoethanol, 0.2 mg/ml DNase, 0.2 mg/ml RNase, 0.35 mg/ml lysozyme) and disrupted by a French press (9,000 psi, eight passages, SLM Amico, SLM Instruments Inc.). Cell debris was removed by centrifugation and protein concentrations were determined by Bradford assay. Protein concentrations were adjusted to 4 mg/ml with wash buffer (100 mM Tris/HCl, pH 8, 150 mM NaCl, 1 mM EDTA). Strep-Tactin® Sepharose material (100 µl bed volume, iba) was filled into reaction vessels and washed with 500 µl wash buffer. For all washes, the material was harvested by centrifugation (4° C., 1000×g, 30 s) and the supernatant was discarded. The material was mixed with 500 µl cell lysate and either no additional compound, 200 µM biotin or 200 µM DS50 as controls, and with 200 µM biotin-DS50, respectively. After incubation on ice for 3 h, the cell lysate was removed by centrifugation and the material washed four times with wash buffer. Specifically bound proteins were eluted with 50 µl SDS-PAGE sample buffer (50 mM Tris/HCl, pH 6.8, 2% sodium dodecyl sulfate (SDS), 10% glycerol, 0.1% bromophenol blue) at 96° C. for 15 min. Proteins were separated using 12% SDS gels according to standard protocols and visualized via ruthenium(II)tris (4,7-diphenyl-1,10-phenantrolinedisulfonate) staining (RuBPS).

Identification of Interaction Partners Via Chromatographic Co-Elution

Logarithmically growing cells of *Bacillus subtilis* 168 were aerobically grown in BMM with 0.78 mM tryptophan at 37° C., harvested by centrifugation and washed (0.02 M Tris/HCl pH 7.5, 0.2 M NaCl). The cells were resuspended in 10 ml lysis buffer (20 mM Tris/HCl, pH 7.5, 0.2 mg/ml DNase, 0.2 mg/ml RNase, 0.2 mg/ml lysozyme, 1 mM DTT, 1 mM β-mercaptoethanol), disrupted with a French press (900 psi, 4° C.), and cell debris was separated via centrifugation (43,000×g, 30 min, 4° C.). The supernatant was concentrated using Amicon® Ultra centrifuge filters (3 kDa exclusion size, Sigma Aldrich), adjusted to a protein concentration of 21.6 mg/ml in 50% glycerol, and stored as aliquots of 300 µl at −80° C.

An aliquot of the protein extract was incubated with 200 µM DS50 for 3 h on ice. A solution of 200 µM DS50 without protein extract served as control. Prior to ion exchange chromatography, the samples were sterile-filtered using "Syringeless Filters-Mini-UniPrep Filter Vials" (GE Healthcare). The samples were separated by an already published method[37] using an UltiMate 3000 UHPLC system (Thermo Fisher Scientific Inc) via a PoiyCATWAX mixed bed ion exchange column (length, 200 mm; particle size, 5 µm; pore size, 1000 Å; PolyLC Inc.). A low salt buffer (buffer A; 13.7 mM Tris, 500 µM DTT, 0.01% $NaN_3$, 1 M HCl, 5% glycerol in *A. dest.*) and a high salt buffer (buffer B; buffer A, with 1.5 M NaCl) were used for elution with the following gradient: initial, 0% buffer B; 5 min, 0% buffer B; 20 min, 10% buffer B; 40 min, 35% buffer B; 90 min, 60% buffer B; 95 min, 100% buffer B; 115 min, 100% buffer B; 120 min, 0% buffer B; 125 min, 0% buffer B with a flow rate of 0.25 ml/min. Fractions were collected in 96 well microtiter plates for 96 min (1 min/fraction).

To quantify DS50, 50 µl of each HPLC fraction was mixed with 100 µl methanol and incubated overnight at −80° C. After a centrifugation step (3,200×g, 20 min, 4° C.), 100 µl of the supernatant were transferred to a new microtiter plate and mass spectrometrically analyzed using a Synapt G2-S (Waters) equipped with an ESI-LockSpray™ source (Waters) and an ACQUITY UPLC®-M-Class-CSH C18 column (pore size, 130 Å; particle size, 1.7 µm; length, 100 mm; Waters). Buffer A (0.1% formic acid in *A. dest.*) and buffer B (0.1% formic acid in acetonitrile) were used as eluents for chromatography. The UPLC was operated with a flow rate of 5 µl/min and a column temperature of 40° C. using the following gradients: initial, 5% buffer B; 15 min, 99% B; 16 min, 99% B; 17 min, 5% B; 25 min, 5% B. Spectra were recorded in positive sensitivity mode with the following settings: Capillary voltage, 3 kV; cone voltage, 30 V; source temperature, 100° C.; cone gas flow, 50 L/h; desolvation flow, 500 L/h; desolvation temperature, 150° C. MSMS spectra of the precursor mass 571.1 were recorded in the mass range 50-1200 m/z with a scanning time of 1 s and a collision energy of 10-35 eV. Leucine-enkephalin was injected as attractant with a capillary voltage of 3 kV. The data were recorded using the program MassLynx™ (Waters). The corresponding program TargetLynx™ was used to quantify DS50 with the following settings: Quantification fragment, 543.1010; retention time, 13.0215 min; retention time window, ±1 min. Serial dilutions of DS50 in methanol were used as quantification standard.

In order to identify proteins in selected fractions, protein concentrations were first determined using the Bradford assay. The proteins were precipitated with 10% (v/v) ice-cold trichloroacetic acid overnight at 4° C. and then centrifuged (16,100×g, 20 min, 4° C.). The protein pellets were incubated with 0.3 ml ice cold acetone at −20° C. for 30 min, centrifuged again and the supernatant was discarded. The pellets were briefly washed two times with acetone, allowed to dry, and resuspended in 50 mM triethyl ammonium bicarbonate buffer. The protein concentration was adjusted to 1 mg/ml using the highest concentrated fraction. Prior to tryptic digestion, the proteins were reduced with 10 mM dithiotreitol (1 h, 60° C.) and alkylated with 5 mM iodoacetamide (15 min, 25° C.). Trypsin (Promega) was added in an enzyme to substrate ratio of 1:100 and the proteins were digested overnight at 37° C. while shaken lightly. The tryptic digestion was terminated with 1 µl trifluoric acid and a Hi3 quantification standard was added (PhosB peptides, waters, final concentration 12.5 fmol/µl). Protein identification by mass spectrometry was performed as described below.

Proteome Analysis Via 2D-PAGE

*B. subtilis* was grown to an $OD_{500}$ of 0.35 in BMM and treated with 3 µg/ml DS50 or 12 µg/ml biotin-DS50 for 15 min or left untreated as control. The following concentrations were used for the reference antibiotics: 0.15 µg/ml nocathiacin I, 8 µg/ml GE2270 A or 50 µg/ml kirromycin. Radioactive labelling of newly synthesized proteins during antibiotic treatment with $^{35}$S-methionine and 2D-PAGE analysis were essentially performed as described[38].

Protein Identification Via Mass Spectrometry

Protein spots were cut out of the gel and decolorized twice in a washing solution (20 mM ammonium bicarbonate, 30% acetonitrile). Disulfide bridges in proteins from gel pieces obtained from 1D-PAGE gels were reduced with 10 mM DTT in wash solution at 60° C. for 45 min. Cysteine alkylation was then performed with 50 mM iodoacetamide (IAA) in a washing solution for 25 min at room temperature in the dark. The gel pieces were washed twice with washing solution for 5 min at room temperature. The reduction and alkylation steps were omitted for samples from 2D-PAGE experiments. All gel pieces were dried using a vacuum centrifuge at 50° C. prior to tryptic digestion with 6.25 ng/µl Trypsin (Promega) in a washing solution for 16 h at 37° C. Tryptic peptides were eluted using 20 µl 0.1% trifluoroacetic acid in an ultrasonic bath for 15 min. The samples were purified using a nanoACQUITY UPLC® Trap Column Symmetry® C18 column (pore size, 100 Å, particle size, 5 µm, length, 20 mm, Waters) at a flow rate of 10 µl/min in 0.5% Buffer B. Tryptic peptides were then eluted from a NanoACQUITY UPLC® CSH130 C18 column (pore size, 130 Å, particle size, 1.7 µm, length, 100 mm; Waters) at a flow rate of 0.35 µl/min at 40° C. using the following gradients. Gradient for identification of proteins from 1D-PAGE: initial, 0.5% eluant B (0.1% formic acid (FA) in acetonitrile); 1 min, 0.5% eluant B; 45 min, 60% eluant B; 48 min, 90% eluant B; 49 min, 99% eluant B; 51 min, 99% eluant B; 52 min, 0.5% eluant B; 60 min, 0.5% eluant B. 0.1% FA in water served as eluent A. Gradient for the identification of proteins from 2D-PAGE: initial, 0.5% eluent B; 22 min, 50% eluent B; 23 min, 99% eluent B; 26 min, 99% eluent B; 27 min, 0.5% eluent B; 30 min, 0.5% eluent B. Continuous $MS^E$ spectra were recorded in a mass range of 50-1200 m/z and with a scanning time of is in positive resolution mode with the following settings: Capillary voltage, 1.7 kV; cone voltage, 30 V; source temperature, 100° C.; cone gas flow, 50 l/h; desolvation gas flow, 500 l/h; desolvation temperature, 150° C. The collision energy was increased from 14 to 45 eV. As mass reference, leucine-enkephalin was injected with a capillary voltage of 3 kV every 60 s. The mass spectra were processed with ProteinLynx Global Server (Waters, version 2.5.2). The processing parameters were adjusted as follows: chromatographic peak width, automatic; MS TOF resolution, automatic; attractant mass for charge 1, 556.2771 Da/e; mass window, 0.25 Da; low energy intensity limit, 50 counts; high energy intensity limit, 15 counts; intensity limit, 500 counts. For protein identification, a database with 4180 proteins of *B. subtilis* was used (NCBI reference sequence: NC_000964.3, manually added: trypsin, keratin, quantification standard PhosB). The following settings were used: Peptide Tolerance, automatic; Fragment Tolerance, automatic; Min. fragment ions per peptide, 2; Min. fragment ions per protein, 6; maximum protein mass, 300.000; primary digestive reagent, trypsin; secondary digestive reagent, none; missed interfaces, 1; fixed modifications, carbamidomethyl C; variable modifications, deamidation N, deamidation Q, oxidation M; false positive rate, 4; quantification standard concentration, 50 fmol.

Example 1: Synthesis and Characterization of Compounds

A template-based synthetic approach used by Liu et al. to obtain one of the first Re(I) carbene complexes was modified.[7] This approach allows the formation of a carbene unit from rhenium-bound CO ligands. In particular, 2-azidoaniline with triphenylphosphine was used to form phosphinimine 2a. This in turn reacts with $Re(CO)_5Br$ at room temperature to convert one of the rhenium-bound CO ligands into a benzimidazol-2-ylidene ligand, which leads to the neutral Re(I) carbene complex 3a with good yield (FIG. 1). It is remarkable that phosphinimine 2a is stable for several weeks in air and at room temperature.

Figure 2:
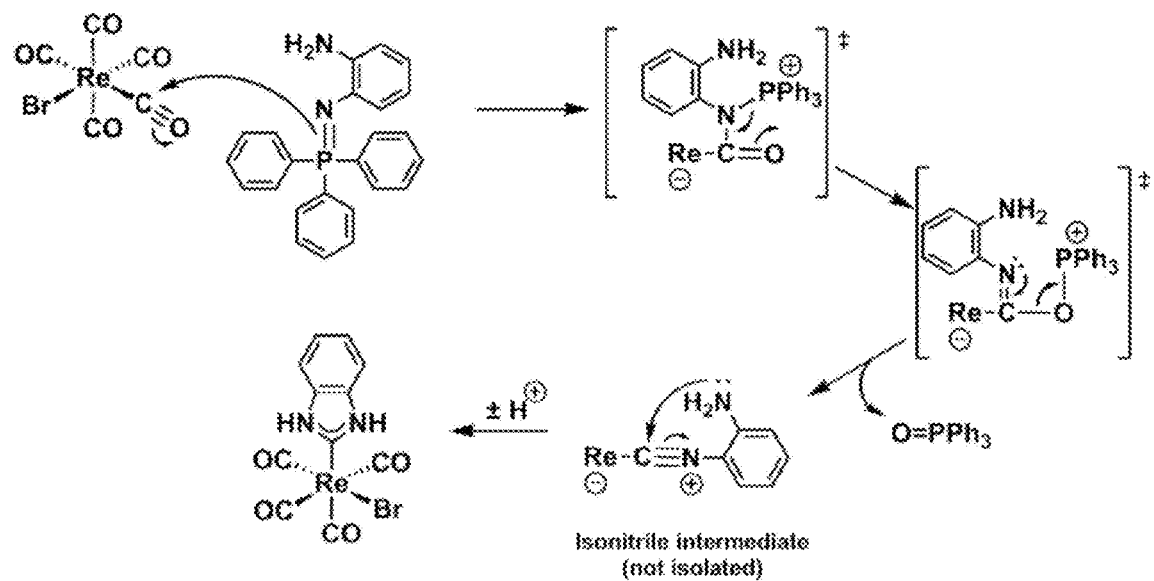

This reaction probably proceeds in two steps. Initially, a metal-bonded CO ligand is deoxygenated by the phosphinimine, and an isonitrile intermediate is formed while releasing $Ph_3PO$. The isonitrile is cyclised due to an intramolecular attack of the adjacent amine to form the desired carbene (FIG. 2).[34,37-38]

The $^1$H-NMR spectrum of 3a shows a characteristic signal for the resulting carbene-NH protons at 10.4 ppm, suggesting the formation of the symmetrical N-unsubstituted carbene. Furthermore, the aromatic protons are now recognizable as a set of two signals at 7.57 and 7.40 ppm. The successful formation of this structure is further supported by $^{13}$C-NMR spectroscopy, which shows the carbene C atom at 171.9 ppm. The successful synthesis of the target compound could also be confirmed by crystal structure analysis.

Figure 3:
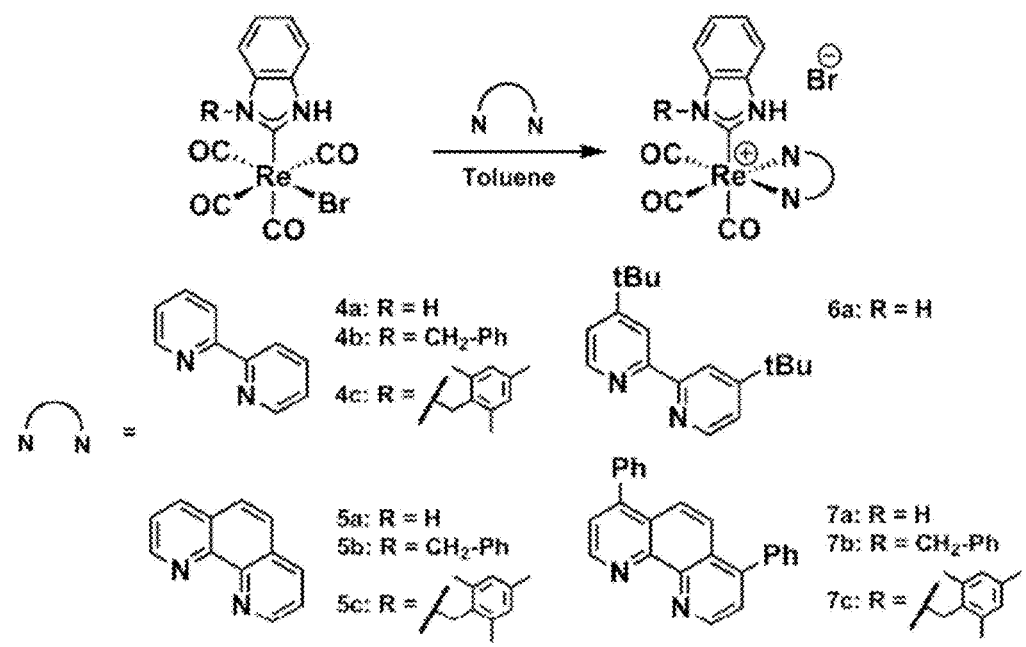
FIG. 3: Ligand exchange reactions of complexes 3a, 3b and 3c.

For biological studies, cationic complexes appear to be useful, so that in 3a a CO and the halide ligand were replaced with different bisimine ligands. In general, this reaction proceeds within 4 hours in toluene. The corresponding cationic Re(I)(NHC) bisimine complexes are obtained with high purity and good yields in the form of yellowish solids after washing with cold ether (FIG. 3).

Figure 4:
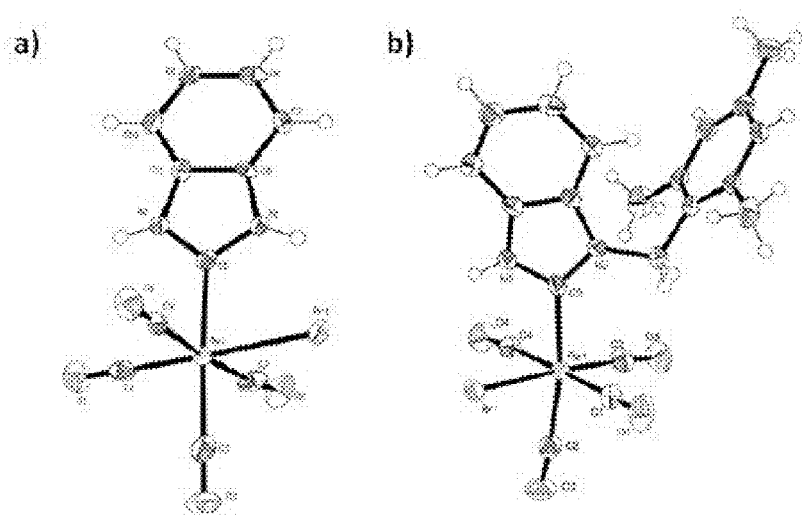
FIG. 4: ORTEP representation of compounds 3a (a) and 3c (b) (ellipsoids are represented with 50% probability of residence).

In order to extend the synthetic range of the described template synthesis to the formation of N-substituted carbene complexes from metal bound CO ligands, additional benzyl or 2,4,6-trimethylbenzyl radicals were added to the initial phosphinimine (FIG. 4). To this end, 2-azidoaniline was reacted with benzaldehyde (or 2,4,6-trimethylbenzaldehyde) and $NaBH(OAc)_3$ to obtain products 1b and 1c via reductive amination. After the reaction with triphenylphosphine and $Re(CO)_5Br$, as described above, the N-benzyl-benzimidazol-2-ylidene (3b) and N-(2,4,6-trimethylbenzyl)benzimidazol-2-ylidene (3c) complexes were obtained with good yields (FIG. 1). The formation of the desired complexes was verified by $^1$H-NMR spectroscopy, finding characteristic signals for the carben-NH protons with a total integral of 1 at 11.35 ppm and 11.27 ppm, respectively. The successful introduction of the aromatic residues is clearly verified, given the occurrence of the benzyl $CH_2$ groups and the additional aromatic protons in the $^1$H-NMR spectra. In order to compare the additional influence of the aromatic groups in biological experiments, 3b and 3c were reacted with the same bisimine as 3a, resulting in complexes 4b-7b and 4c-7c.

Example 2: X-Ray Crystallography

Suitable single crystals for X-ray structure analysis of the neutral complexes 3a and 3c were obtained via slow evaporation of solutions in DCM. ORTEP representations of the complexes are shown in FIG. 4. Both complexes assume a distorted octadric structure while maintaining facial coordination geometry, which underlines the selective attack of the phosphinimine on the carbonyl ligands. The rhenium-carbene bond lengths are in the range between 2.169 and 2.179 Å, while the Re—CO bond lengths vary between 1.915 and 2.024 Å. This is in line with previously published Re(I) carbene complexes.[7-8] Interestingly, the additional aromatic unit in 3c leads to a more pronounced distortion of the octahedral rhenium environment as compared to 3a.

This is shown by comparing the $C_{carbene}$—Re—CO angle, which decreases from 177.1° (3a) to 169.8° (3c). This may be due to repulsive interactions resulting from the introduction of bulky aromatic substituents and their electronic influence on the carbene group.

Figure 5:
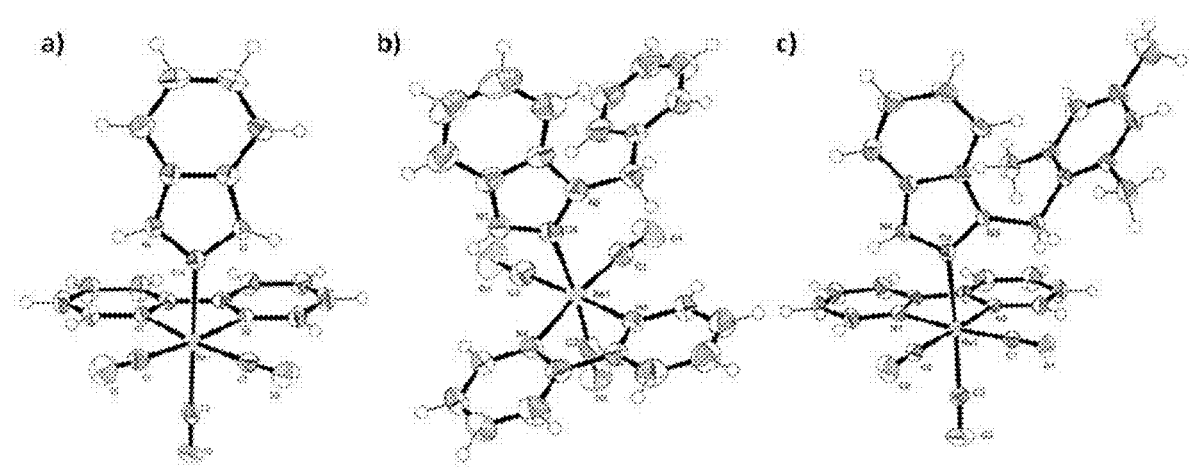
FIG. 5: ORTEP representation of the bipyridine complexes 4a (a), 4b (b) and 4c (c) (ellipsoids are represented with 50% probability of residence). The counterion bromide was not included in the figure for clarity reasons.

Crystals of cationic complexes 4a, 5a, 6a, 4b, and 4c were obtained by slowly evaporating a solution of the complexes in a mixture of dichloromethane and hexane or via slow diffusion of ether into a methanolic solution. The molecular structures of the complexes containing bipyridine are shown in FIG. 5. The structures obtained prove the facial arrangement of the CO ligands in the reaction with the corresponding bisimine ligands. As expected, the former Re bound bromide atom is found as counterion of the cationic complexes. All complexes show distorted octahedral geometry. After coordination of the bisimine ligands, however, the $C_{carbene}$—Re—CO angles with 173.95 (4b) to 177.14 Å (4a) are in a narrower range as compared to the neutral counterparts. The average Re—CO bond lengths decrease to values between 1,912-1,972 Å. The structures obtained are very similar to related compounds.[7]

Example 3: Absorption and Emission Properties

As one might expect for many $d^6$-Re(I)(CO)$_3$ complexes, the carbene complexes show an extensive photophysical behavior that has attracted considerable attention in recent years. The available results are summarized in FIG. 6.

Figures 7, 8:
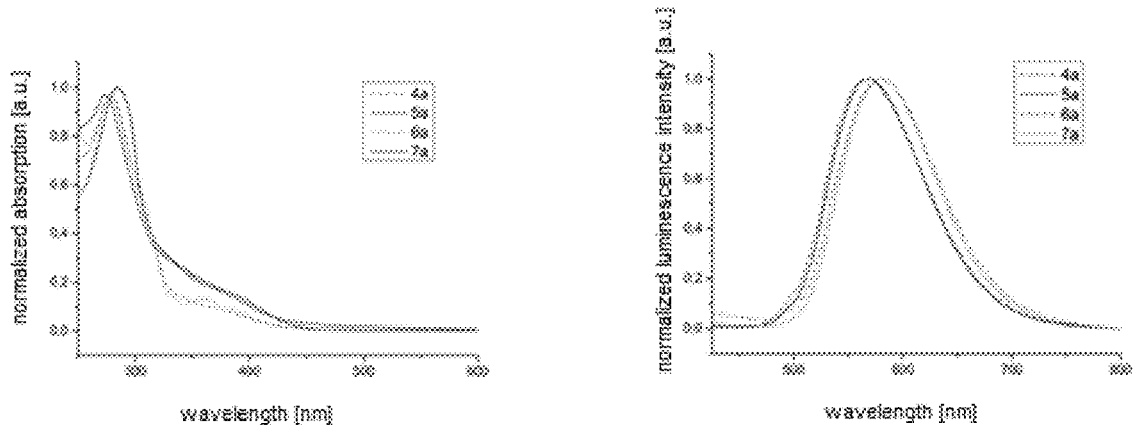
FIG. 7: Normalized absorption (left) and emission spectra (right) of compounds 4a, 5a, 6a, and 7a in acetonitrile.
FIG. 8: Minimum inhibitory concentrations (MHK) of 3a and the complex series 4, 5, and 7 against Gram-positive strains. Values are given in μM. The complexes show no antimicrobial activity against Gram-negative strains.

In general, the tested complexes behave very similarly and exhibit very distinct and intense absorption bands in the UV range at about 280 nm with extinction coefficients of about $10^4$ dm$^3$M$^{-1}$ cm$^{-1}$ (FIG. 7, left-hand side). These bands are attributed to the intense intraligand-transitions of the bisimine ligands (LC, $\pi$-$\pi$*) and are often found in Re(I)(CO)$_3$-bisimine complexes. The less intensively wide absorption bands of about 330 to 450 nm with extinction coefficients around $10^3$ dm$^3$M$^{-1}$ cm$^{-1}$ probably result from MLCT transitions (d(Re)→$\pi$*(Bisimin)).[43,44]

Excitation at 350 nm leads to large Stokes shifts and emission in the yellow region of the visible spectrum with emission bands between 550-580 nm in acetonitrile and water for all cationic complexes (FIG. 7, right-hand side). These structureless emission bands probably result from emitting $^3$MLCT states (d(Re)→$\pi$*(Bisimin)), which, after excitation, result from occupied $^1$MLCT/$^1$LC states via intersystem crossing.[44] The luminescence lifetime is in the range of several hundred nanoseconds with an increase of 66 ns (4a) to 224 ns (7a) in acetonitrile and thus in accordance with $^3$MLCT states. Not all lifetimes correspond to exclusively monoexponential decay curves, so that a further state, presumably a short-lived $^3$LC state, is proposed. Since charge transfer states are usually strongly influenced by the polarity of the environment, CT nature can be observed by shifting the emission maxima when changing the solvent. 4a and 5a show a very slight redshift when water is used instead of acetonitrile. However, the maxima of the complexes 6a and 7a are subject to a pronounced hypsochromic shift to 530 and 553 nm, respectively. To further investigate the nature of the excited states, the inventors measured the luminescence lifetime of complexes 4a and 5a in degassed acetonitrile. In both cases, an approximate doubling of the lifetime compared to the non-degassed solution is observed. This confirms that the emission states of the complexes most likely correspond to a triplet nature, as these are known to be susceptible to quenching by oxygen. Quantum yields ranged from 1.8% to 4.9%, which are very comparable to related Re(I) bisimine and carbene complexes.[8,39,44] Considering the structureless bands, the emission of the complexes mainly results from $^3$MLCT states with minor contributions from $^3$LC states. Together with the large Stokes shifts, it seems likely that localization of the compounds based on fluorescence microscopy is possible in a biological environment.

Example 4: Antimicrobial Activity

The antimicrobial activity of complexes with either bipyridine, phenanthroline or badophenanthroline ligands was investigated by determining the minimum inhibitory concentration (MHK) against a representative selection of Gram-positive and Gram-negative bacterial strains. B. subtilis and two strains of S. aureus (WT and MRSA) served as Gram-positive test strains, while E. coli, A. baumannii and P. aeruginosa were selected as Gram-negative strains. Serial dilutions of the complexes were prepared in Mueller Hinton liquid medium, inoculated with 5×10$^5$ bacteria per ml and incubated at 37° C. for 18 h. The lowest concentration that inhibits visible growth was defined as the minimum inhibitory concentration. The MHK values obtained are summarized in FIG. 8.

All compounds tested were inactive against the Gram-negative bacterial strains tested. However, the complexes showed activity against the tested Gram-positive bacterial strains with MHK values in the very low micromolar range. A general trend in the set of agents is an increase in activity when the carbene-nitrogen substituent is changed from H to benzyl (a<b). The trimethylbenzyl-substituted series (c) is among the most active compounds in the study in cases of 4c and 5c, whereas 7c is less active. This is consistent with the hypothesis that total activity correlates with lipophilicity. On the one hand, the activity of the compounds can be increased to some extent by increasing lipophilicity (e.g. series a<b, 4a<5a<7a and 4b<5b<5c). On the other hand, excessive lipophilicity may lead to reduced activity. This is most evident for the compounds of series 7, where the order of activity is reversed compared to their lipophilicity. While 7c is the most lipophilic compound, it is less active than 7b and 7a (7c<7b<7a). One possible explanation may be the increasingly poor solubility in aqueous solution. It is also noteworthy that minor changes in molecular structure (3a/4a) lead to dramatic differences in activity. Not surprisingly it is to be noted that different model strains react differently to different complexes. S. aureus ATCC 3300 seems to be able to withstand the bathophenanthrolin-containing complexes (c) much better than the other strains.

Example 5: Range of Antibacterial Activity of DS50 and Biotin-DS50

Figures 9, 10:
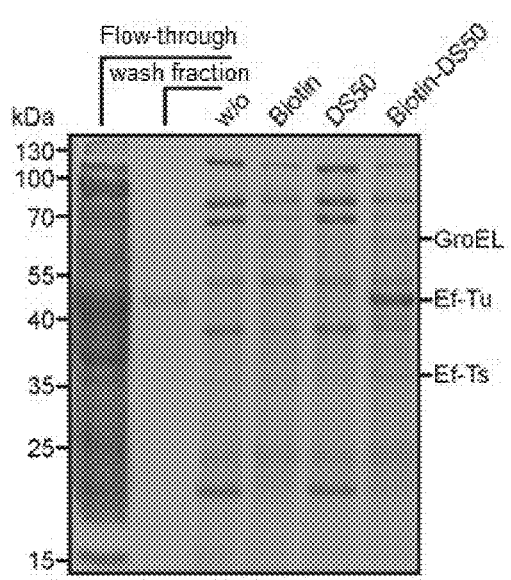
FIG. 9: Antibacterial activity of DS50 and biotin-DS50. The minimum inhibitory concentration (μM) of both compounds was determined against a selection of Gram-positive and Gram-negative bacteria in Mueller-Hinton medium in a microtiter plate assay.
FIG. 10: The elongation factor Tu of B. subtilis binds to immobilized biotin DS50. Biotin-DS50 was immobilized with Strep-Tactin® Sepharose and incubated with protein extract of B. subtilis. Unbound proteins (flow-through) were discarded and the sepharose was washed (wash fraction) before proteins bound to biotin DS50 were eluted by heating in SDS-PAGE sample buffers. In parallel, Strep-Tactin® Sepharose was incubated with biotin, DS50 or without complex (w/o) for control. Proteins that specifically bind to biotin-DS50 were identified by mass spectrometry.

DS50 was selected as an example to address the mechanism of action of the substances. A biotinylated derivative of DS50 (biotin-DS50) was prepared and used for the analysis of interaction partners. First, it was determined whether the biotinylation has an effect on the antibacterial activity of DS50. The lowest concentration of a compound that inhibits the visible growth of bacteria is defined as minimum inhibitory concentration (MHK) and is a measure of the antibacterial activity of a compound. The MHK of DS50 and its biotinylated derivative was measured against a set of Gram-negative and Gram-positive bacteria using a standardized microplate assay. DS50 showed weak or no activity against Gram-negative bacteria, but was effective against Gram-positive bacteria with MHKs in the low µg/ml range (FIG. 9). The MHK against methicillin-resistant *Staphylococcus aureus* (MRSA) was 4 µg/ml. Biotinylation of DS50 for target identification studies via immobilization leads to a slight decrease in antimicrobial activity, but this compound was still active against Gram-positive bacteria (16-32 µg/ml). Therefore, biotin-DS50 was used for target identification experiments. Whether the slight decrease in antibacterial activity is caused by reduced uptake of biotin-DS50 or by interference with target interaction remains uninvestigated.

Example 6: Target Identification Experiments with Biotin-DS50

Biotinylated DS50 was immobilized using Strep-Tactin® Sepharose material and incubated with cytosolic cell extract of the Gram-positive bacterium *Bacillus subtilis*. Unbound proteins were removed by washing and proteins bound to biotin-DS50 were eluted by boiling in SDS-PAGE sample buffer. Strep-Tactin® Sepharose was incubated with biotin, with non-biotinylated DS50 or without compound as controls. The elution fractions were separated by SDS-PAGE and the proteins were visualized by RuBPs staining (FIG. 10). Compared to the controls, a very prominent protein band at immobilized biotin-DS50 was identified as elongation factor Tu (EF-Tu). Two bands that co-eluted to a lesser extent and that could be additional target proteins or interaction partners of EF-Tu are the chaperone subunit GroEL and the elongation factor Ts (EF-Ts). It is known that the nucleotide exchange factor EF-Ts interacts with EF-Tu. A direct interaction between GroEL and EF-Tu has not yet been demonstrated. Additional bands that occur in all samples are likely to be naturally biotinylated proteins that can bind directly to the material.

Example 7: Mode of Action of DS50 and Biotin-DS50

Figure 11:
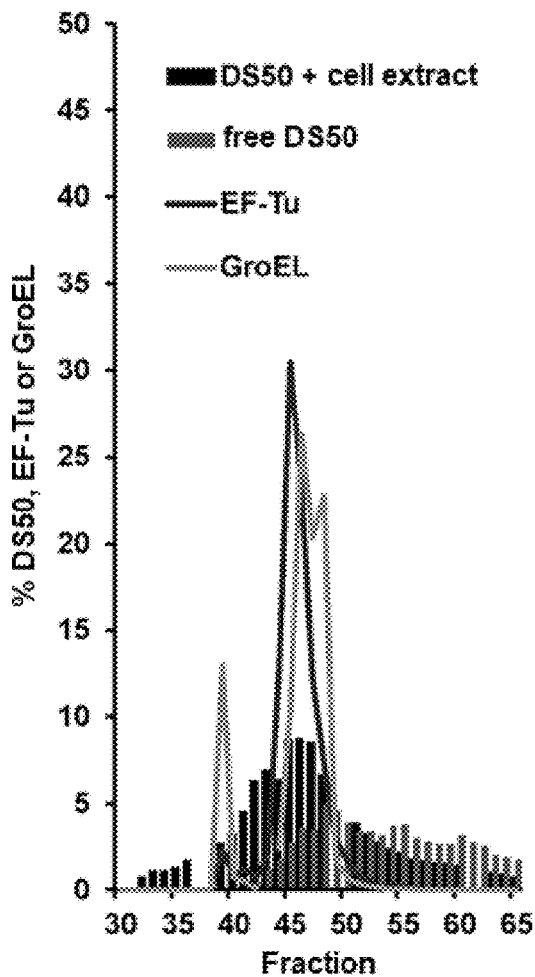
FIG. 11: The elongation factor Tu and GroEL from B. subtilis co-elute with DS50. DS50 was incubated with cytosolic protein extract of B. subtilis or with buffer as control (free compound). The extract was separated by native ion exchange chromatography and elution profiles of the free and protein-bound DS50 were reconstituted by mass spectrometry. Proteins in fractions containing protein-bound DS50 were identified. The elution profiles of elongation factor Tu and GroEL are shown.

In order to check whether EF-Tu is also the target of non-biotinylated DS50, a chromatographic co-elution experiment was performed. For this purpose, DS50 was incubated with a cytosolic protein extract of *B. subtilis* and with buffer, respectively. Both samples were separated by native ion exchange chromatography and 96 fractions were collected for each run. DS50 was quantified in the collected fractions using LC-MS to identify protein-bound (DS50+ cell extract) and free DS50 (incubated with buffer). Incubation of DS50 with the cell lysate led to a shift in retention time compared to the free agent (FIG. 11). Using LC-MS, proteins in fractions with shifted DS50 were identified and elution profiles of EF-Tu and GroEL are shown. Both EF-Tu and GroEL co-eluted with DS50, while EF-Ts was not identified in these fractions. Thus, binding of DS50 to the EF-Tu elongation factor could thus be confirmed.

Figure 12:
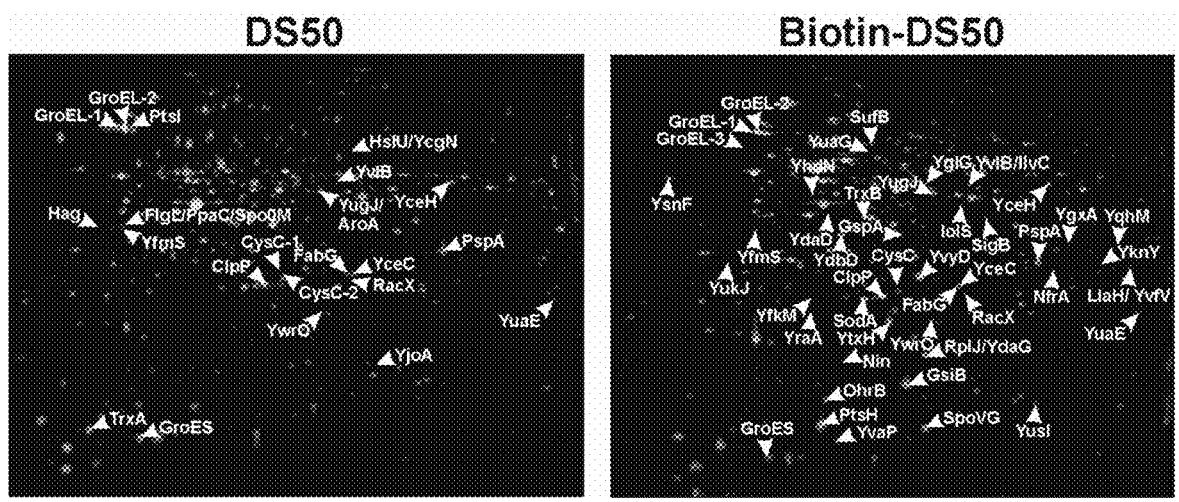
FIG. 12: Proteome profile of B. subtilis after treatment with DS50 or biotin-DS50. Logarithmically growing cells of B. subtilis were subjected to stress by treatment with antibiotics or grown untreated as a control. Newly synthesized proteins were radioactively labelled and the proteins were separated by 2D polyacrylamide gel electrophoresis. Radioactively labelled proteins were detected using phosphoscreens and phosphoscanners, and the digitalized gel images of the untreated controls (green) were superimposed with gel images of the antibiotic treatment (red). Up, down and non-regulated proteins appear in red, green and yellow, respectively. Marker proteins that have been upregulated at least twice in all biological replicas in response to antibiotic treatment and identified by mass spectrometry are indicated by arrows.

In response to stress, such as the addition of antibiotics, the proteome of a cell is specifically adapted to counteract and survive stress. The upregulated proteins are very specific to the mode of action of the antibiotic used[39]. Therefore, the comparison of the proteome profile of *B. subtilis* after treatment with DS50 or biotin-DS50 can reveal whether the mode of action is altered by biotinylation. For proteome analysis, *B. subtilis* was treated with DS50 or left untreated as a control. Newly synthesized proteins were radioactively labelled and separated by 2D gel electrophoresis using the isoelectric point and the molecular weight in the first and second dimension, respectively. Radioactively labelled proteins were visualized and false color images of the gels of a control sample and a sample obtained after antibiotic treatment were superimposed (FIG. 12). Software-based analyses were used to define marker proteins for both substances, which were upregulated by a factor of at least two in all biological replicas after antibiotic treatment, and identified by mass spectrometry. Although more marker proteins are upregulated after treatment with biotin-DS50, both substances show a high congruence with regard to marker proteins. Furthermore, many of the marker proteins are also upregulated for DS50 after biotin-DS50 treatment, but do not reach the strict threshold value. This indicates that biotinylation, in principle, preserves the mode of action.

Example 8: Proteome Analysis for Determining the Mode of Action

In order to analyze whether DS50 has the same mode of action as well characterized EF-Tu inhibitors, further comparative proteome analyses were performed. The most studied EF-Tu attacking antibiotics so far are the thiazolyl peptides nocathiacin I and GE2270 A as well as the structurally unrelated kirromycin. Nocathiacin I binds to the ribosome and inhibits GTP hydrolysis of EF-Tu and other GTP-dependent translation factors[40]. GE2270 A inhibits the binding of EF-Tu to Phe-tRNA$^{Phe}$ [41], and the formation of a complex of kirromycin with EF-Tu●GDP●aatRNA blocks the detachment of the elongation factor from the ribosome[42].

Figure 13:
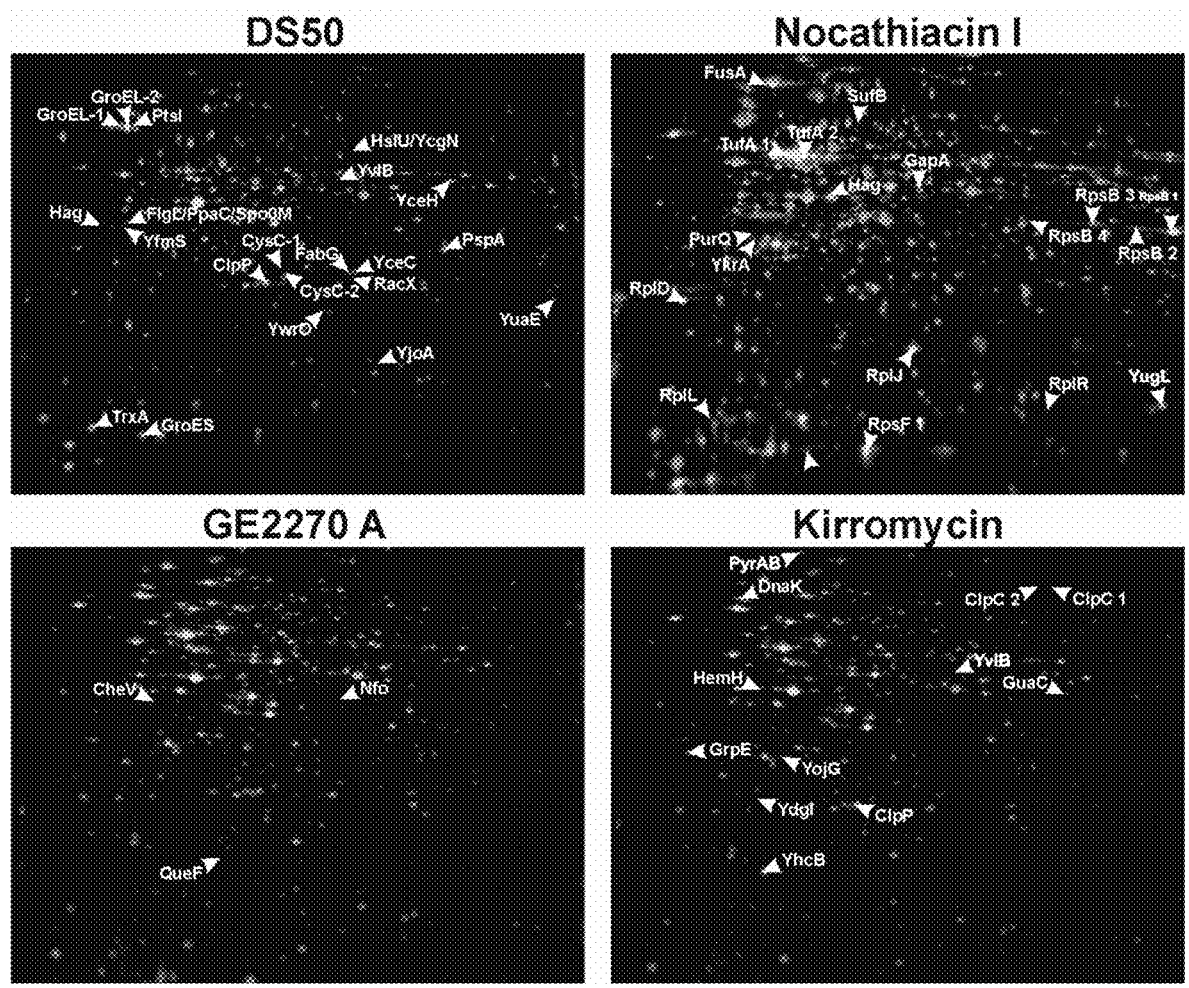
FIG. 13: Proteome profile of B. subtilis after treatment with DS50 or antibiotics known to interfere with the translational activity of elongation factor Tu (nocathiazine I, GE2270 A and kirromycin). Logarithmically growing cells of B. subtilis were subjected to stress by treatment with antibiotics or grown untreated as control. Newly synthesized proteins were radioactively labelled and the proteins were separated by 2D polyacrylamide gel electrophoresis. Newly synthesized proteins were shown in false color images as described above. The untreated controls (green) were superimposed with antibiotic treatment gels (red). Up, down and non-regulated proteins appear in red, green and yellow, respectively. Marker proteins that were upregulated at least twice in all biological replicas in response to antibiotic treatment were identified by mass spectrometry and are indicated by arrows.

The proteome analyses were performed as described above. The proteome response to DS50 was compared with the response to antibiotics known to interfere with EF-Tu activity (FIG. 13). DS50, nocathiacin I, GE2270 A and kirromycin show very different proteome profiles, reflecting different modes of action. After treatment with nocathiacin I, protein biosynthesis decreases to −15% (data not shown) compared to control conditions, and many ribosomal proteins and elongation factors such as EF-Tu (TufA) and EF-G (FusA) are upregulated. In response to GE2270 A, protein biosynthesis is reduced to −65% and only a few marker proteins are upregulated, of which only the enzyme QueF is associated with translation. Protein biosynthesis was not affected by kirromycin and the proteome profile mainly shows the induction of proteins involved in protein quality control, such as the chaperones DnaK and GrpE or the protease subunits ClpC and ClpP.

Treatment of *B. subtilis* with DS50 reduces protein biosynthesis to −67% and 21 marker proteins are induced. Like kirromycin, DS50 induces marker proteins necessary for protein quality control, but the induced proteins are different and include the chaperone system GroESL and the protease subunits ClpY and ClpP. Overall, the proteome profile of DS50 does not match that of the reference antibiotics, indicating that the mode of action is different. In addition, only DS50 treatment induces PspA, a marker protein for membrane stress, and YuaE, which is upregulated in response to membrane-active antibiotics. In addition, DS50 has lytic effects on *B. subtilis* cells in higher concentrations (data not shown).

The complexes have been described broadly and generically herein. Each of the narrower species and subgeneric groupings falling within the generic disclosure also form part of the complex. This includes the generic description of the invention with a proviso or negative limitation removing any subject-matter from the genus, regardless of whether or not the excised material is specifically recited herein. Other embodiments are within the following claims. In addition, where features or aspects of the complex are described in terms of Markush groups, those skilled in the art would recognize that the complex is also thereby described in terms of any individual member or subgroup of members of the Markush group.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the complex disclosed herein without departing from the scope and spirit of the invention. The compositions, methods, procedures, treatments, molecules and specific compounds described herein are presently representative of non-limiting embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," containing", etc. shall be read expansively and without limitation. The word "comprise" or variations such as "comprises" or "comprising" will accordingly be understood to imply the inclusion of a stated integer or groups of integers but not the exclusion of any other integer or group of integers. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The content of all documents and patent documents cited herein is incorporated by reference in their entirety.

REFERENCES

1 S. Diez-Gonzalez, N. Marion and S. P. Nolan, *Chem. Rev.*, 2009, 109, 3612-3676.
2 M. N. Hopkinson, C. Richter, M. Schedler and F. Glorius, *Nature*, 2014, 510, 485-496.
3 R. Visbal and M. Concepcion Gimeno, *Chem. Soc. Rev.*, 2014, 43, 3551-3574.
4 L. Oehninger, R. Rubbiani and I. Ott, *Dalton Trans.*, 2013, 42, 3269-3284.
5 M.-L. Teyssot, A.-S. Jarrousse, M. Manin, A. Chevry, S. Roche, F. Norre, C. Beaudoin, L. Morel, D. Boyer, R. Mahiou and A. Gautier, *Dalton Trans*, 2009, 6894-6902.
6 K. M. Hindi, M. J. Panzner, C. A. Tessier, C. L. Cannon and W. J. Youngs, *Chem. Rev.* 2009, 109, 3859-3884.
7 C.-Y. Liu, D.-Y. Chen, G.-H. Lee, S.-M. Peng and S.-T. Liu, *Organometallics*, 1996, 15, 1055-1061.
8 W.-M. Xue, M. C.-W. Chan, Z.-M. Su, K.-K. Cheung, S.-T. Liu and C.-M. Che, *Organometallics*, 1998, 17, 1622-1630.
9 C.-H. Chen, Y.-H. Liu, S.-M. Peng, J.-T. Chen and S.-T. Liu, *Dalton Trans.*, 2012, 41, 2747-2754.
10 C.-O. Ng, S.-M. Yiu and C.-H. Ko, *Inorg Chem.*, 2014, 53, 3022-3031.
11 O. Hiltner, E. Herdtweck, M. Drees, W. A. Herrmann and F. E. Kuhn, *Eur. J. Inorg. Chem.* 2009, 1825-1831.
12 M. A. Huertos, J. Perez, L. Riera, J. Diaz and R. Lopez, *Chem. Eur. J.*, 2010, 16, 8495-8507.
13 V. Blase, T. Pape and F. E. Hahn, *J. Organomet. Chem.*, 2011, 696, 3337-3342.
14 T. A. Martin, C. E. Ellul, M. F. Mahon, M. E. Warren, D. Allan and M. K. Whittlesey, *Organometallics*, 2011, 30, 2200-2211.
15 W. A. Herrmann, D. Mihalios, K. Ofele, P. Kiprof and F. Belmedjahed, *Chem. Ber.* 1992, 125, 1795-1799.
16 D. Canella, S. J. Hock, O. Hiltner, E. Herdtweck, W. A. Herrmann and F. E. Kuhn, *Dalton Trans.*, 2012, 41, 2110-2121.
17 S. J. Hock, L.-A. Schaper, A. Pothig, M. Drees, E. Herdtweck, O. Hiltner, W. A. Herrmann and F. E. Kuhn, *Dalton Trans.* 2014, 43, 2259-2271.
18 C. Y. Chan and P. J. Barnard, *Dalton Trans.*, 2015, 44, 19126-19140.
19 A. J. Huckaba, E. A. Sharpe and J. H. Delcamp, *Inorg. Chem.*, 2016, 55, 682-690.
20 L. A. Casson, S. Muzzioli, P. Raiteri, B. W. Skelton, S. Stagni, M. Massi and D. H. Brown, *Dalton Trans.*, 2011, 40, 11960-11967.
21 X.-W. $L_1$, H.-Y. $L_1$, G.-F. Wang, F. Chen, Y.-Z. $L_1$, X.-T. Chen, Y.-X. Zheng and Z.-L. Xue, *Organometallics*, 2012, 31, 3829-3835.
22 C. Hille and F. E. Kuhn, *Dalton Trans.* 2016, 45, 15-31.
23 S. J. Hock, L.-A. Schaper, W. A. Herrmann and F. E. Kuhn, *Chem. Soc. Rev.* 2013, 42, 5073.
24 A. Leonidova and G. Gasser, *ACS Chem. Biol.* 2014, 9, 2180-2193.
25 K. K.-W. Lo, K. Y. Zhang and S. P.-Y. $L_1$, *Eur. J Inorg. Chem.* 2011, 3551-3568.
26 S. Jurgens, W. A. Herrmann and F. E. Kuhn, *J. organomet. Chem.*, 2014, 751, 83-89.
27 M. Wenzel, M. Patra, C. H. R. Senges, I. Ott, J. J. Stepanek, A. Pinto, P. Prochnow, C. Vuong, S. Langklotz, N. Metzler-Nolte and J. E. Bandow, *ACS Chem. Biol.*, 2013, 8(7), 1442-1450.
28 M. Patra, G. Gasser and N. Metzler-Nolte, *Dalton Trans.*, 2012, 41, 6350-6358.
29 Y. Gothe, T. Marzo, L. Messori and N. Metzler-Nolte, *Chem. Eur. J.*, 2016, 22(35), 12487-12494.
30 Y. Gothe, T. Marzo, L. Messori and N. Metzler-Nolte, *Chem. Commun.*, 2015, 51(15), 3151-3153.
31 F. E. Hahn and M. C. Jahnke, *Angew. Chem. Int. Ed.* 2008, 47, 3122-3172.
32 A. Flores-Figueroa, O. Kaufhold, K. O. Feldmann and F. E. Hahn, *Dalton Trans.*, 2009, 9334-9342.

33 F. E. Hahn, V. Langenhahn, N. Meier, T. Lugger and W. P. Fehlhammer, *Chem. Eur. J.*, 2003, 9(3), 704-712.
34 M. C. Jahnke and F. E. Hahn, *Chem. Lett.*, 2015, 44, 226-237.
35 C.-C. Ko, C.-O. Ng and S.-M. Yiu, *Organometallics*, 2012, 31, 7074-7084.
36 A. W.-Y. Cheung, L. T.-L. Lo, C.-C. Ko and S.-M. Yiu, *Inorg. Chem.*, 2011, 50, 4798-4810.
37 J. N. Y. Chan et al, 2012, *Mol Cell Proteomics*
38 M. Wenzel et al. *Antimicrobial Agents and Chemotherapy* 55, 2590-2596 (2011)
39 J. E. Bandow et al. *Antimicrobial Agents and Chemotherapy* 47, 948-955 (2003)
40 M. J. Pucci et al. *Antimicrobial Agents and Chemotherapy* 48, 3697-3701 (2004)
41 P. H. Anborgh and A. Parmeggiani, *The Journal of biological chemistry* 268, 24622-24628 (1993)
42 H. Wolf, G. Chinali and A. Parmeggiani, *European Journal of Biochemistry* 75, 67-75 (1977))

The invention claimed is:

1. A complex having the structure of formula (I)

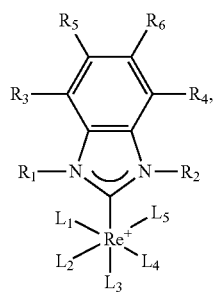

wherein
$R_1$, $R_2$, $R_3$, $R_4$, $R_5$, and $R_6$ are independently selected from the group consisting of H; linear or branched, substituted or unsubstituted alkyl; linear or branched, substituted or unsubstituted heteroalkyl; linear or branched, substituted or unsubstituted alkenyl; linear or branched, substituted or unsubstituted heteroalkenyl; linear or branched, substituted or unsubstituted alkynyl; linear or branched, substituted or unsubstituted heteroalkynyl; substituted or unsubstituted cycloalkyl; substituted or unsubstituted heterocycloalkyl; substituted or unsubstituted aryl; substituted or unsubstituted heteroaryl; linear or branched, substituted or unsubstituted alkylaryl; or linear or branched, substituted or unsubstituted heteroalkylaryl; wherein each of these groups has up to 20 carbon atoms; and
$L_1$, $L_2$, $L_3$, $L_4$, and $L_5$ are independently metal-coordinating ligands selected from the group consisting of neutral ligands, anionic ligands, and mixed ligands; wherein $L_1$, $L_2$, $L_3$, $L_4$, and $L_5$ form one or more of a monodentate ligand, one or more of a bidentate ligand, a tridentate ligand, a tetradentate ligand, a pentadentate ligand, and combinations thereof.

2. The complex according to claim 1, wherein
a) $L_1$, $L_2$, $L_3$, $L_4$, and $L_5$ are independently selected from the group consisting of halo, carbonyl, $C_1$-$C_{10}$ alkyl, $C_1$-$C_{10}$ alkoxy, sulfides, thiocyanates, nitrates, azides, fluorides, hydroxide ion, $H_2O$, nitrites, isothiocyanates, acetonitrile, pyridines, ammonia, triphenylphosphines, cyanides, carbon monoxide, linear or branched, substituted or unsubstituted alkene having up to 20 carbon atoms, benzene, cyclopentadienyl, nitrosyl, oxoligand, sulfites, tricyclohexylphosphane, trimethylphosphane, tri(o-tolyl)phosphane, cycloheptatriene, carbon dioxide; or b) two or three of $L_1$, $L_2$, $L_3$, $L_4$, and $L_5$ are linked to form a molecule selected from the group consisting of oxalates, ethylenediamine, 2,2' bipyridine, 1,10-phenanthroline, acetylacetonate, aminopolycarboxylic acids, 1,2-bis(diphenylphosphino)ethane, 1,1-bis(diphenylphosphino)methane, diethylenetriamine, dimethylglyoximate, glycine, iminodiacetic acid, nitrilotriacetic acid, pyrazine, scorpion ligands, 2,2',6',2''-Terpyridine, triazacyclononane, di-(2-picolyl)amines, 2,2'-dipyridylamines, tris(2-pyridylmethyl)amines, N,N,N',N'-tetramethylethyleneediamine (TMEDA), N-propyl(2-pyridyl)methanimine (NPrPMI),

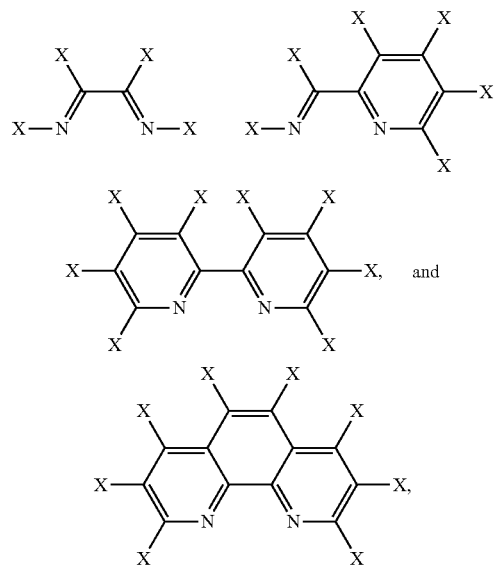

wherein each X is independently H or a linear or branched alkyl having up to 20 carbon atoms; and
wherein $L_1$, $L_2$, $L_3$, $L_4$, and $L_5$, which are not linked to other metal-coordinating ligands, are defined as in a).

3. The complex of claim 1, wherein $L_4$ and $L_5$ are linked to form a molecule and are selected from the group consisting of

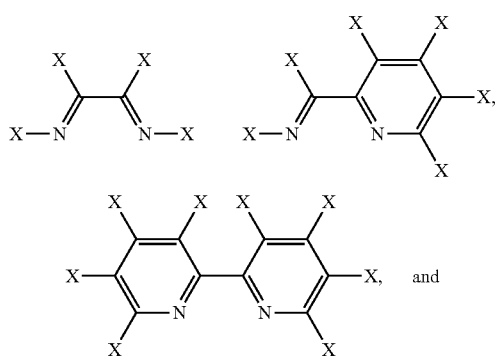

-continued

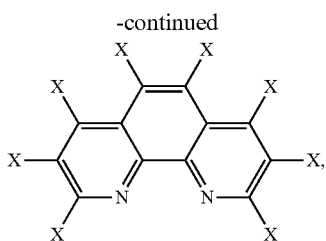

wherein each X is independently H or a linear or branched alkyl having up to 20 carbon atoms.

4. The complex according to claim 3, wherein $L_4$ and $L_5$ are selected from the group consisting of

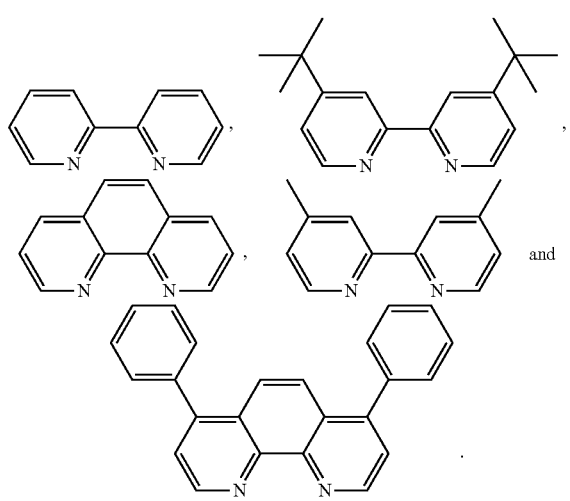

5. The complex according to claim 1, wherein $R_1$ is H, CH$_2$-phenyl, or

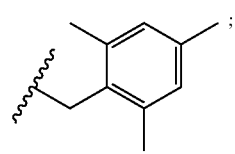 [SMILES: *Cc1c(C)cc(C)cc1C]

and/or $R_2$ is H.

6. The complex according to claim 1, wherein a) $R_3$-$R_6$ are H; and/or b) $L_1$-$L_3$ are CO.

7. The complex according to claim 1, wherein a) $R_1$ is H, CH$_2$-phenyl, or and $R_2$ is H; and $R_3$-$R_6$ are H; and $L_1$-$L_3$ are CO; and $L_4$ and $L_5$ are linked to form

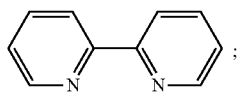 [SMILES: c1ccc(-c2ccccn2)nc1]

or b) $R_1$ is H, CH$_2$-phenyl, or

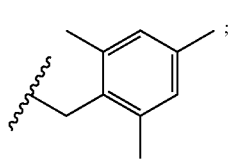

and $R_2$ is H; and $R_3$-$R_6$ are H; and $L_1$-$L_3$ are CO; and $L_4$ and $L_5$ are linked to form

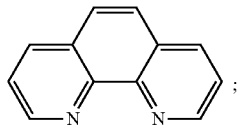

or c) $R_1$ is H; and $R_2$ is H; and $R_3$-$R_6$ are H; and $L_1$-$L_3$ are CO; and $L_4$ and $L_5$ are linked to form

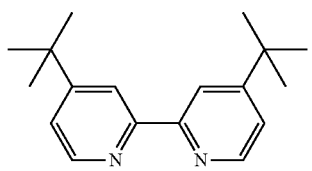

or d) $R_1$ is H, CH$_2$-phenyl, or

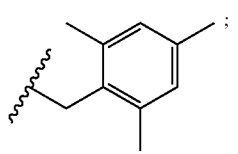 [SMILES: *Cc1c(C)cc(C)cc1C]

and
R$_2$ is H; and
R$_3$-R$_6$ are H; and
L$_1$-L$_3$ are CO; and
L$_4$ and L$_5$ are linked to form

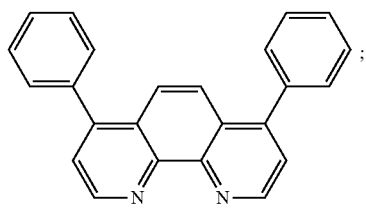 [SMILES: c1ccc(-c2ccnc3c2ccc2c(-c4ccccc4)ccnc23)cc1]

or
e) R$_1$ is H; and
R$_2$ is H; and
R$_3$-R$_6$ are H; and
L$_1$-L$_3$ are CO; and
L$_4$ and L$_5$ are linked to form

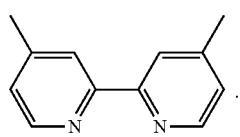

8. A pharmaceutical composition comprising a complex according to claim 1 and further comprising a pharmaceutically acceptable carrier or excipient.

9. A process for preparing a complex having the structure of formula (II)

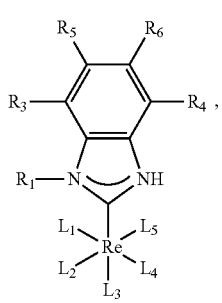

wherein
R$_1$, R$_3$, R$_4$, R$_5$, and R$_6$ are independently selected from the group consisting of H, linear or branched, substituted or unsubstituted alkyl; linear or branched, substituted or unsubstituted heteroalkyl; linear or branched, substituted or unsubstituted alkenyl; linear or branched, substituted or unsubstituted heteroalkenyl; linear or branched, substituted or unsubstituted alkynyl; substituted or unsubstituted heteroalkynyl; substituted or unsubstituted cycloalkyl; substituted or unsubstituted heterocycloalkyl; substituted or unsubstituted aryl; substituted or unsubstituted heteroaryl; linear or branched, substituted or unsubstituted alkylaryl; linear or branched, substituted or unsubstituted heteroalkylaryl; wherein each of these groups having up to 20 carbon atoms; and L$_1$, L$_2$, L$_3$, L$_4$, and L$_5$ are independently metal-coordinating ligands selected from the group consisting of neutral ligands, anionic ligands, and mixed ligands; wherein L$_1$, L$_2$, L$_3$, L$_4$, and L$_5$ form one or more of a monodentate ligand, one or more of a bidentate ligand, a tridentate ligand, a tetradentate ligand, a pentadentate ligand, and combinations thereof;
wherein the method comprises:
contacting a compound having the structure of formula (III)

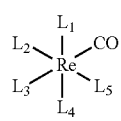

with a compound having the structure of formula (IV)

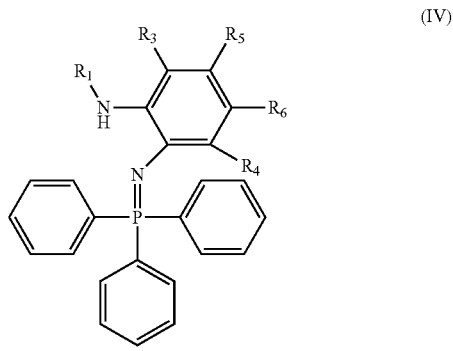

to form the complex having the structure of formula (II).

10. A method for identifying a molecule, which interacts with a complex according to claim 1, wherein the method comprises:
providing a complex according to claim 1, wherein R$_5$ is a linker group;
immobilizing the complex on a solid support, wherein the solid support binds to the complex via the linker group;
contacting the immobilized complex with a solution comprising molecules of interest;
releasing the molecules interacting with the immobilized complex; and
identifying the released molecules.

11. A method according to claim 10, wherein the linker group is

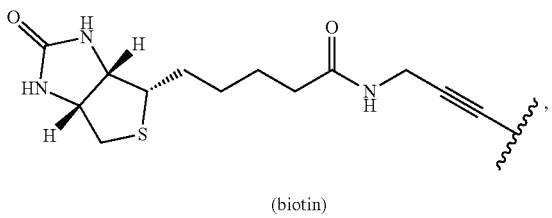 [SMILES: *C#CCNC(=O)CCCC[C@@H]1SC[C@@H]2NC(=O)N[C@@H]21]

(biotin)

and wherein the solid carrier comprises avidin and/or streptavidin.

* * * * *